(12) United States Patent
Porter

(10) Patent No.: US 11,813,414 B2
(45) Date of Patent: Nov. 14, 2023

(54) CONTROL SYSTEMS FOR SHAPEABLE CATHETERS

(71) Applicants: STRYKER CORPORATION, Kalamazoo, MI (US); STRYKER EUROPEAN OPERATIONS LIMITED, Carrigtwohill (IE)

(72) Inventor: Stephen Porter, Piedmont, CA (US)

(73) Assignees: Stryker Corporation, Kalamazoo, MI (US); Stryker European Operations Limited, Carrigtwohill (IE)

(*) Notice: Subject to any disclaimer, the term of this patent is extended or adjusted under 35 U.S.C. 154(b) by 356 days.

(21) Appl. No.: 17/194,198

(22) Filed: Mar. 5, 2021

(65) Prior Publication Data

US 2021/0283373 A1 Sep. 16, 2021

Related U.S. Application Data

(60) Provisional application No. 62/987,680, filed on Mar. 10, 2020.

(51) Int. Cl.
*A61M 25/01* (2006.01)
(52) U.S. Cl.
CPC .... *A61M 25/0147* (2013.01); *A61M 25/0136* (2013.01)
(58) Field of Classification Search
CPC .......... A61M 25/0147; A61M 25/0136; A61M 2025/0161
See application file for complete search history.

(56) References Cited

U.S. PATENT DOCUMENTS

| 5,545,200 | A | * | 8/1996 | West | A61M 25/0136 606/29 |
| 6,033,378 | A | * | 3/2000 | Lundquist | A61M 25/0147 604/95.01 |
| 2005/0288626 | A1 | * | 12/2005 | Koerner | A61M 25/0147 604/95.04 |
| 2005/0288656 | A1 | * | 12/2005 | Koerner | A61M 25/0043 604/95.04 |
| 2006/0084964 | A1 | * | 4/2006 | Knudson | A61M 25/0136 604/95.04 |
| 2010/0280449 | A1 | * | 11/2010 | Alvarez | A61B 34/71 606/1 |
| 2013/0060237 | A1 | * | 3/2013 | Ogle | A61M 25/01 604/528 |

(Continued)

OTHER PUBLICATIONS

PCT International Search Report and Written Opinion for International Appln. No. PCT/US2021/021253, Applicant Stryker Corporation, dated Aug. 26, 2021 (11 pages).

*Primary Examiner* — Tan-Uyen T Ho
*Assistant Examiner* — Theodore Le Vu
(74) *Attorney, Agent, or Firm* — Vista IP Law Group, LLP

(57) ABSTRACT

An intravascular device includes an elongated body having a proximal end and a distal end, and a plurality of energy transmitting conduits extending within the elongated body. The distal ends of the energy transmitting conduits terminate at different axial locations along the distal end of the elongated body. In one embodiment, the number of energy transmission conduits is only two, such that the number of bends in the compound curve assumed by the distal end of the elongated body is only two, although the number of energy transmission conduits may be any suitable number.

10 Claims, 24 Drawing Sheets

(56) References Cited

U.S. PATENT DOCUMENTS

| | | | |
|---|---|---|---|
| 2013/0102960 A1* | 4/2013 | Miyoshi | A61M 25/0136 604/95.04 |
| 2016/0158497 A1* | 6/2016 | Tran | A61M 25/0147 604/95.04 |
| 2017/0065415 A1 | 3/2017 | Rupp et al. | |
| 2018/0071490 A1 | 3/2018 | Khuu et al. | |
| 2020/0061340 A1 | 2/2020 | Mixter et al. | |
| 2020/0214840 A1* | 7/2020 | Rupp | A61F 2/2433 |

\* cited by examiner

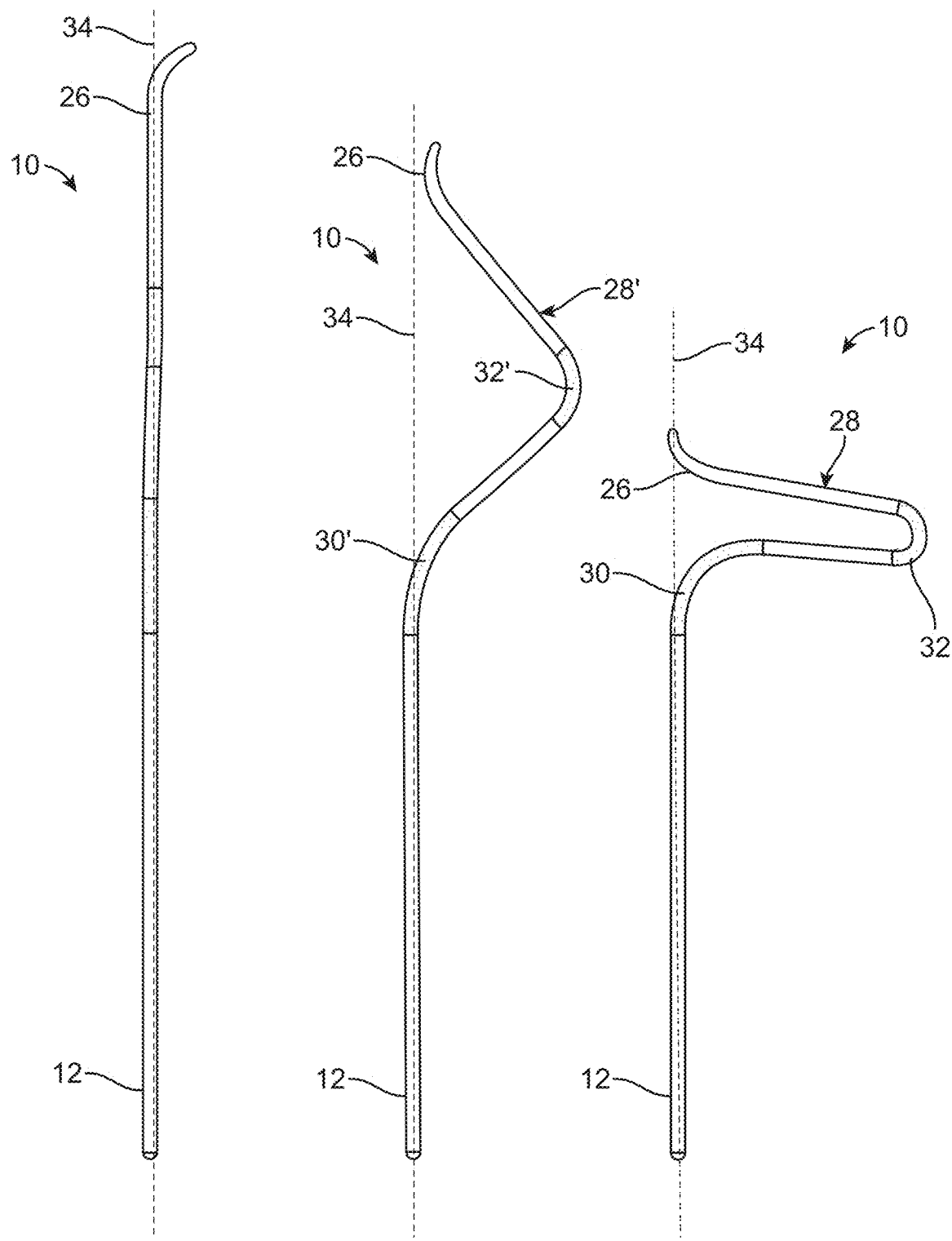

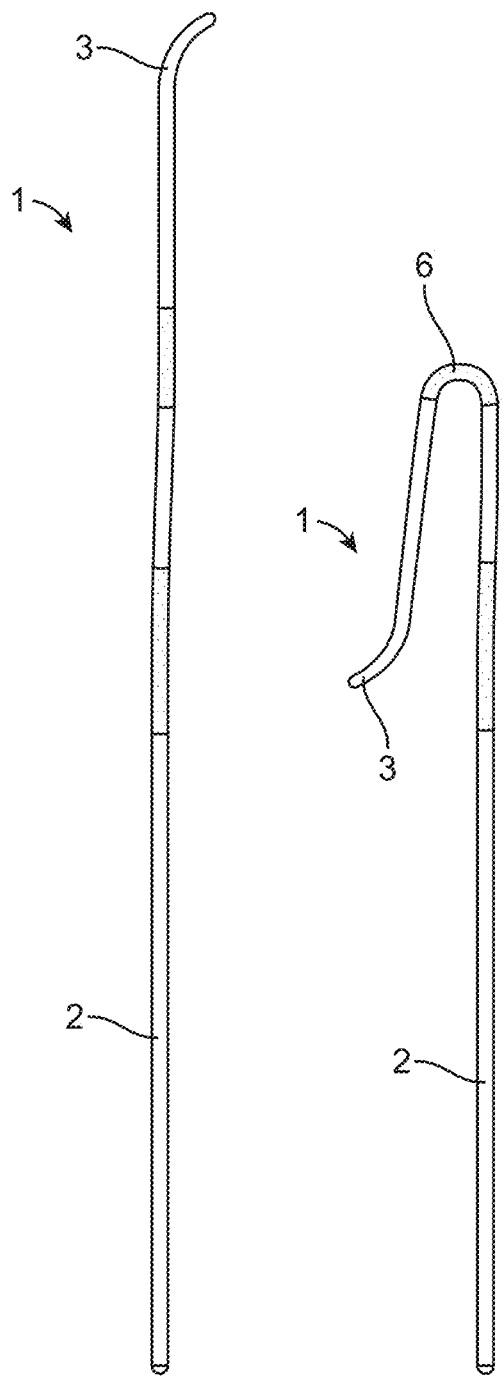
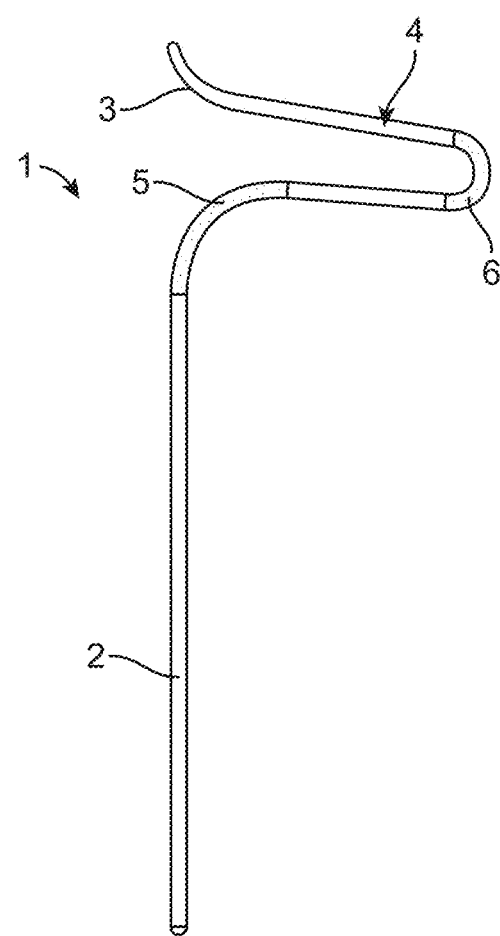
FIG. 3A (PRIOR ART)
FIG. 3B (PRIOR ART)
FIG. 3C (PRIOR ART)

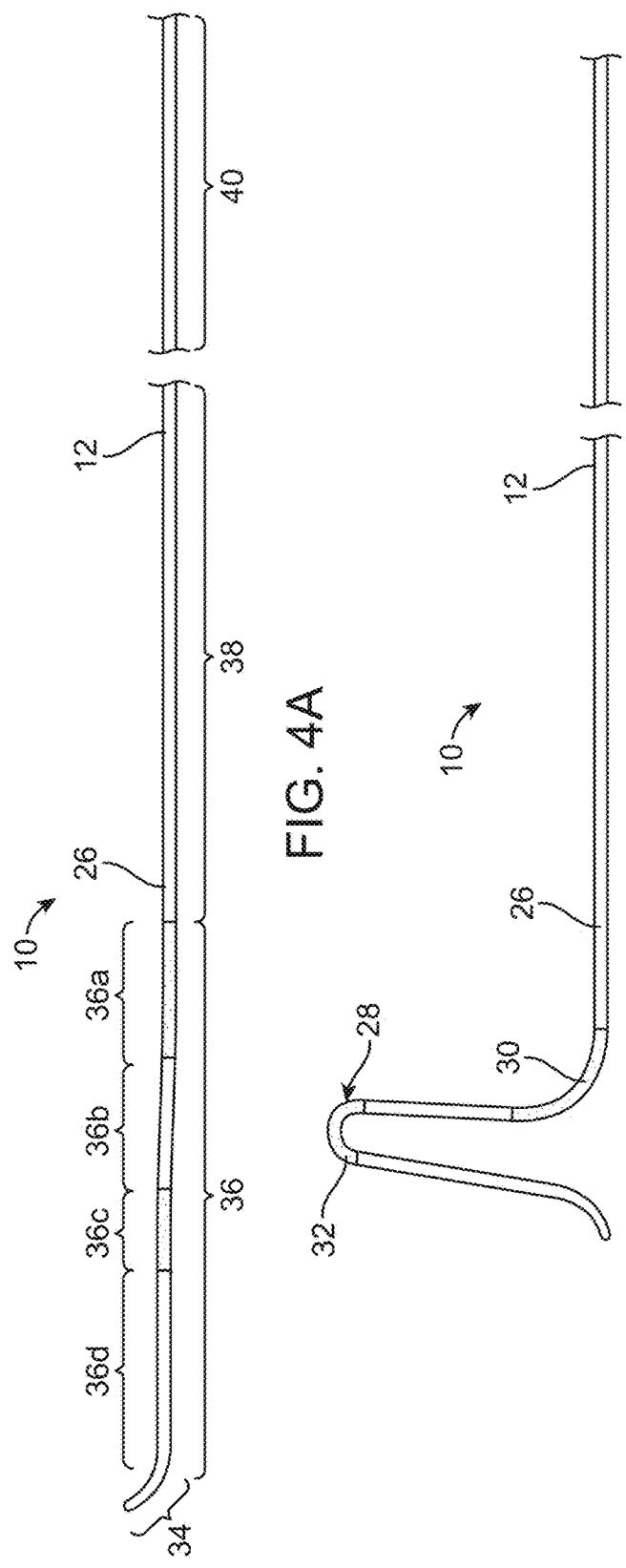
FIG. 4A
FIG. 4B
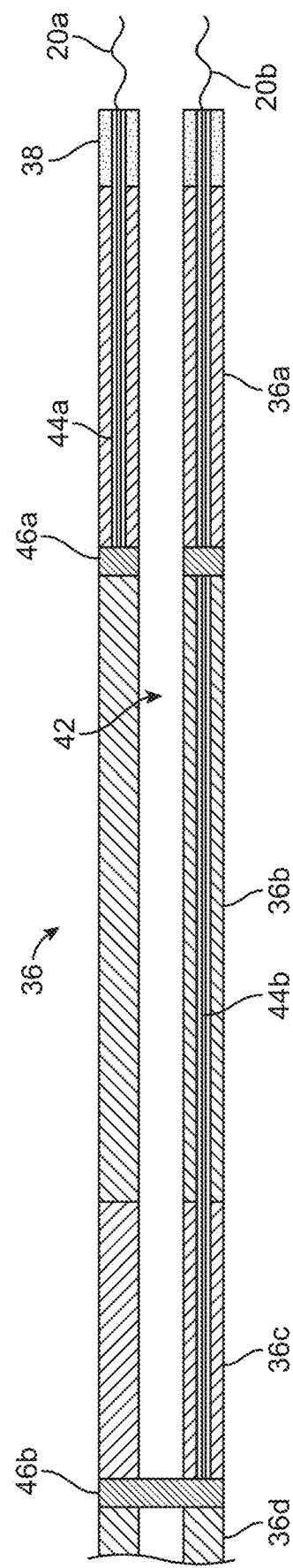
FIG. 4C

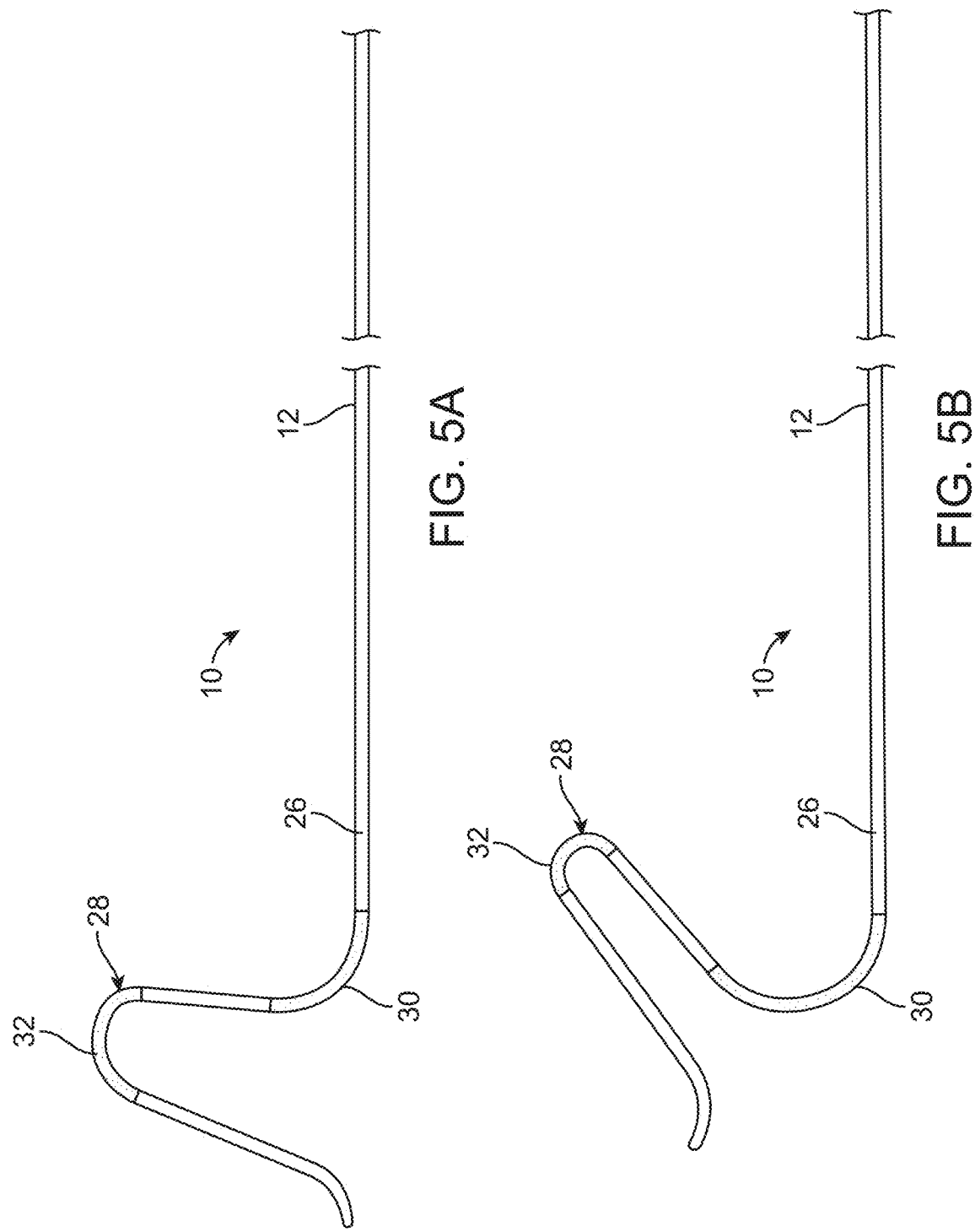

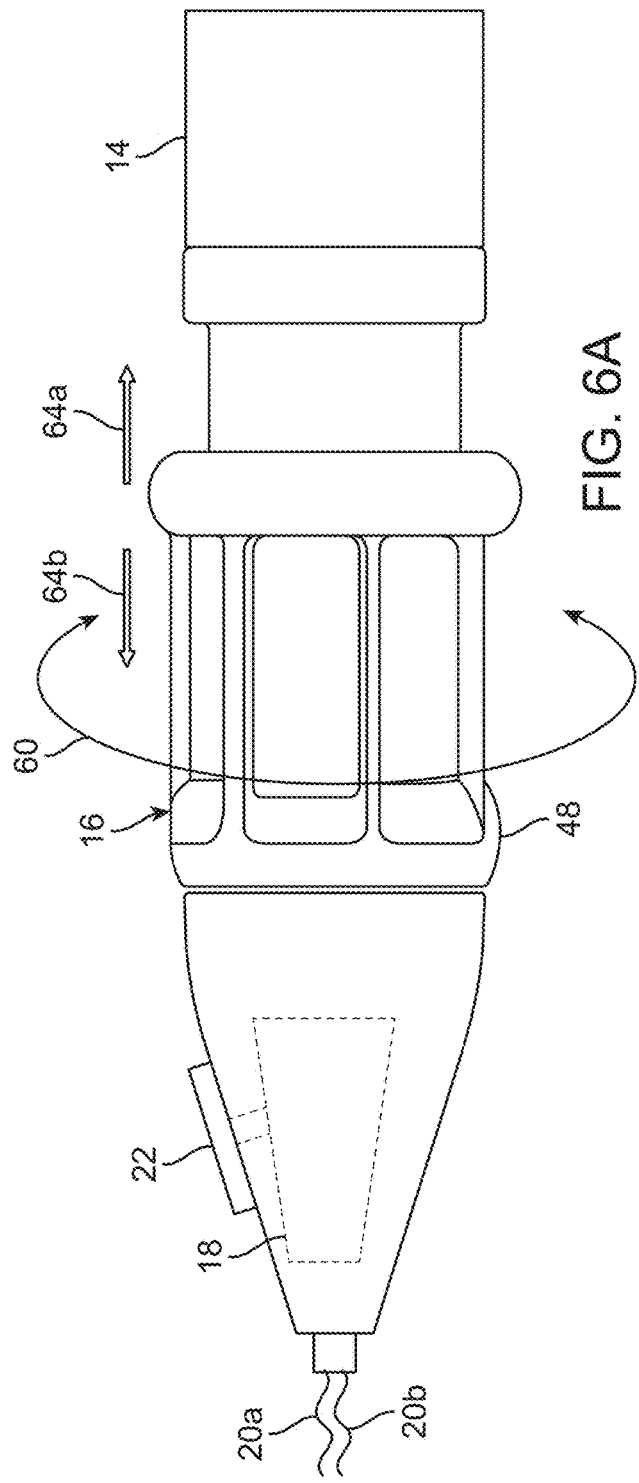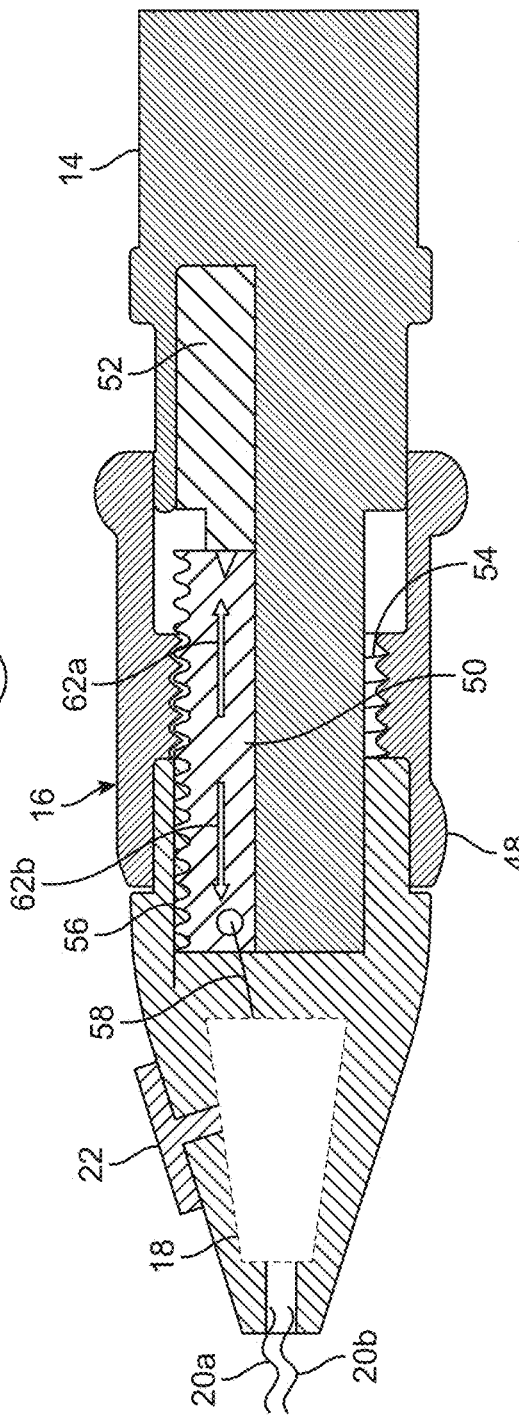

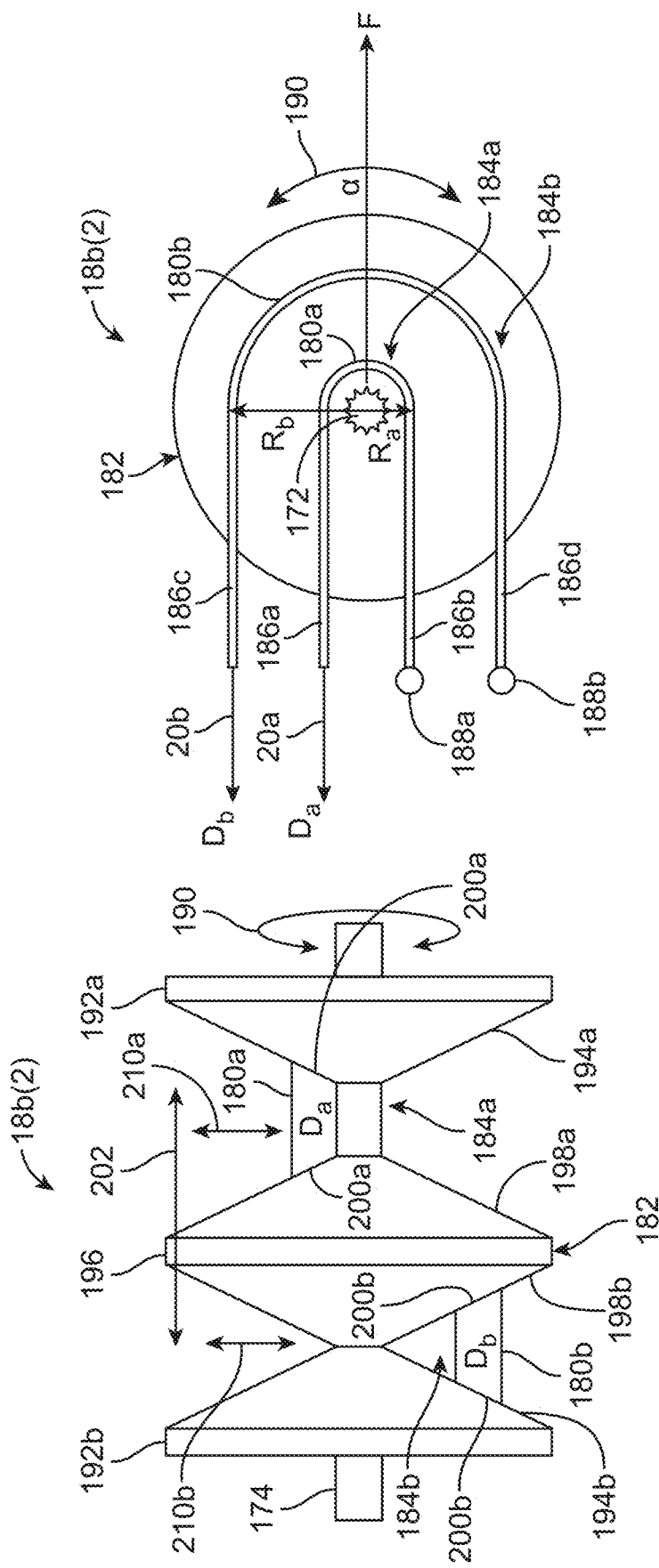

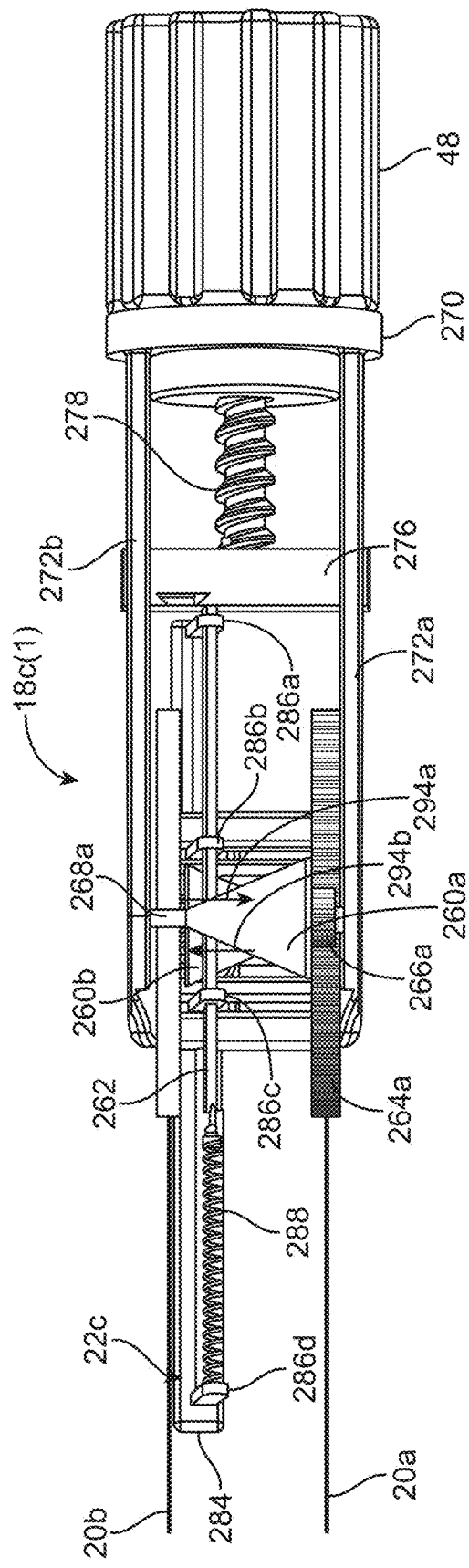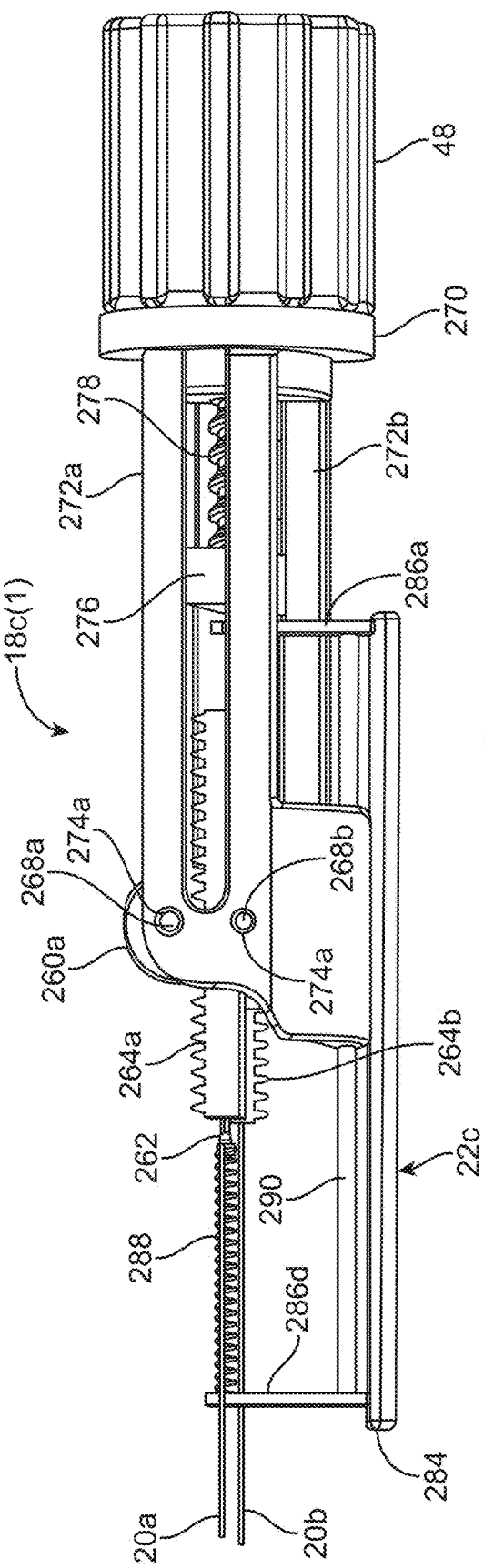
FIG. 20
FIG. 21

CONTROL SYSTEMS FOR SHAPEABLE CATHETERS

RELATED APPLICATION DATA

The present application claims the benefit of priority under 35 U.S.C. § 119 to U.S. provisional patent application Ser. No. 62/987,680, filed Mar. 10, 2020.

FIELD OF THE INVENTION

The present disclosure relates generally to medical devices and intravascular medical procedures and, more particularly, to devices and methods for controlling deflection at the distal end of a catheter.

BACKGROUND

Therapeutic or diagnostic catheters are commonly used to perform medical procedures within very small spaces in a patient's body. Most of these medical procedures mandate precise catheter navigation. To access a target site within the human body from a remote location, a catheter is typically passed through one or more body lumens, such as through the vascular system, to the target site. When the vascular system is used, the catheter is inserted into an artery or vein percutaneously or through a relatively small incision in the patient's body. The catheter is then threaded through the patient's system of blood vessels to reach the desired target site. Often a pathway is created through the vasculature to the target site with the use of a delivery device, such as a guide catheter, through which a therapeutic or diagnostic catheter can be guided to the target site.

The usefulness of guide catheters is limited by their ability to successfully navigate through small vessels and around tight bends in the vasculature, such as around the aortic arch. Access of the great vessels off the aortic arch pose challenges, especially when anatomical features require devices to follow a highly tortured or a not well supported path. To overcome some of these challenges, pre-shaped guide catheters have been developed to direct working catheters, such as therapeutic or diagnostic catheters, that are passed therethrough. Such pre-shaped guide catheters may have multiple axially spaced curves that allow access to the great vessels off of the aortic arch. For example, guide catheters having various types of pre-shaped distal ends (e.g., Simmons, Headhunter, Vitek, Bentson, Newton shapes) have been developed to both assist in negotiating twists and branches common in a patient's arterial or venous system and to maintain a shape once positioned within a target cavity, e.g., a chamber in the heart. However, since the pre-shaped curve is fixed into the guide catheter at the time of manufacture, the radius, extent of the curvature, and overall shape generally cannot be altered. Due to anatomical variations, extensive pre-surgical planning would be necessary to determine the correct curvature of the guide catheter.

New guide catheters that are able to change shape in-situ may be of use in facilitating access to a target site. For example, the distal end of one guide catheter can be in a shaped/stiff configuration to precisely direct a guidewire extending through the guide catheter towards a particular vascular opening. The distal end of the guide catheter can then be transformed to a non-shaped/flexible configuration to allow easier advancement along the guidewire towards and into the vascular opening, which, after removal of the guidewire, then provides support for the advancement of a working catheter through the guide catheter. Conventionally, the distal end of a guide catheter can be made to be selectively shapeable or stiff by deflecting the distal end of the guide catheter.

Some deflectable guide catheters have been developed to more effectively navigate through the tortuous pathways of some body lumens, particularly the vascular system. For example, deflectable guide catheters are commonly used in electrophysiology (EP) for mapping and ablation of endocardial tissue, and structural heart repair (e.g., transcatheter aortic valve repair (TAVR), atrial septal defect and appendage closure, etc.). Deflectable guide catheters used for these applications generally need to provide very stable and finely adjustable positioning in a bi-directional, and sometimes multi-planar, manner to either support working catheters or allow working catheters to precisely contact specific tissues.

Deflectable guide catheters conventionally employ one or more pull wires embedded within the wall of the guide catheter. Typically, the pull wire(s) are embedded within the wall for the entire length of the guide catheter or for most of the length of the guide catheter, from the distal end to one or more control mechanisms on the proximal end of the guide catheter. Various methods for actuation of deflectable and/or tip deflection catheters have been developed, and including individually sliding, pivoting, or rotating means of user force input into the control system to affect a wire tension in the catheter, e.g., as described in U.S. Pat. Nos. 5,190,050 and 6,913,594 and U.S. Patent Publication No. 2017/0065415. For one-way deflections in a single plane, the pull wire or multiple pull wires run down one side of the guide catheter. When the pull wire is pulled the pulling force reduces the length of the guide catheter on the side of the pull wire, thereby causing the guide catheter to bend in that direction. The resilience of the guidewire extending through the guide catheter may return the distal end of the guide catheter to a straight configuration when the pull wire is relaxed. For two-way deflectable guide catheter, a second pull wire may be fitted at 180 degrees from the first wire. In this case the guide catheter will flex in much the same way as per a single direction device as each wire is loaded, with the flexing caused by each wire being in different directions. The wire opposite the active pull wire may either remain stationary relative to the proximal end or it may move proximally as this side of the deflection section also contracts.

Navigation through the lumens of the vascular system typically only requires deflecting the catheter tip toward a particular branch at a bifurcation, a relatively simple maneuver. Such deflection, basically the ability to form a single curvature, is generally inadequate for accessing and directing the catheter into the great vessels of the aortic arch or toward a target in a cavity, such as the heart chamber. For example, in the case of TAVR, when targeting the mitral valve within the cavity of the left atrium or left ventricle, many more variables are present, such as the type of approach, the variability of anatomy and the various targets associated with the mitral valve, such as various points on the leaflets, the commissures, the free edges, the chordae tendinae, etc. These variables increase the need for a deflectable guide catheter that can provide a higher degree of articulation than a single curve catheter or a catheter that does not provide compound curves in an adjustable manner.

Accordingly, deflectable guide catheters capable of providing compound curves in an adjustable manner have been designed. One such deflectable guide catheter employs multiple pull wires that extend along different sides of the catheter and are affixed at different axial locations along the catheter. The pull wires may be tensioned by separate mechanisms at the proximal end of the catheter to cause the distal end of the guide catheter to assume a compound curve, with each bend in the compound curve being independently articulatable by a respective pull wire. However, placing the distal end of such a deflectable catheter into the desired compound curve may be difficult and tedious, since tension must be applied to one pull wire by its control mechanism to create one bend of the compound curve, tension must then be applied to another pull wire by its control mechanism to create another bend of the compound curve, and so forth. Furthermore, tensions on the respective pull wires must be balanced, such that the magnitudes of the bends in the desired compound curve are achieved. Proper balance between the pull wires may be difficult to achieve tension on a distal bend in the compound curve may affect a more proximal bend in the compound curve. Thus, the tensions of independently controllable pull wires of such a guide catheter may have to be repeatedly adjusted back and forth to achieve the desired compound curve.

There, thus, is an ongoing need to provide a simpler and more robust means for creating a compound curve at a distal end of an elongated intravascular device, such as a guide catheter.

SUMMARY

In accordance with the present inventions, an intravascular device comprises an elongated body having a proximal end and a distal end, and a plurality of energy transmitting conduits extending within the elongated body. The distal ends of the energy transmitting conduits terminate at different axial locations along the distal end of the elongated body. In one embodiment, the number of energy transmission conduits is only two, such that the number of bends in the compound curve assumed by the distal end of the elongated body is only two, although the number of energy transmission conduits may be any suitable number.

The intravascular body further comprises a control mechanism, and an energy transmission linkage coupled between proximal ends of the energy transmission conduits and the control mechanism. The energy transmission linkage is configured for, in response to a single energy input applied to the energy transmission linkage by the control mechanism, simultaneously applying a plurality of energy outputs respectively to the proximal ends of the energy transmitting conduits at a preset control parameter ratio. The distal end of the elongated body is configured for assuming a compound curve comprising a plurality of bends in response to the application of the plurality of energy outputs by the energy transmission linkage to the proximal ends of the energy transmitting conduits. The intravascular device may further comprise a handle affixed to the proximal end of elongated body, in which case, the control mechanism and energy transmission linkage may be supported by the handle.

In one embodiment, the control parameter ratio of the energy transmission linkage is different than unity. In another embodiment, the control parameter ratio of the energy transmission linkage is adjustable, in which case, the intravascular device may further comprise a control parameter ratio adjustment mechanism configured for adjusting the preset control parameter ratio of the energy transmission linkage. The control parameter ratio adjustment mechanism may, e.g., be configured for adjusting the preset control parameter ratio of the energy transmission linkage within a continuous range or discrete range.

In one embodiment, the energy transmission conduits may be mechanical energy transmission conduits, in which case, the energy transmission linkage may be a mechanical energy transmission linkage, the single energy input may be a single mechanical energy input, and the energy outputs may be mechanical energy outputs. The mechanical energy outputs may be applied to the proximal ends of the mechanical energy transmission conduits in accordance with one of a preset force ratio and a preset linear displacement ratio.

In one specific embodiment, the mechanical energy transmission conduits are pull wires and the one of the preset force ratio and the preset linear displacement ratio comprises one of a pull wire tension ratio and a pull wire displacement ratio.

If one of the preset pull wire tension ratio and the preset pull wire displacement ratio comprises the preset pull wire tension ratio, the mechanical energy outputs are tensile outputs. In this case, the mechanical transmission linkage may comprise a first moment arm to which a proximal end of a first one of the pull wires is operatively coupled, a second moment arm to which a proximal end of a second one of the pull wires is operatively coupled, and a drive assembly operatively coupled to the first moment arm and the second moment arm. The control mechanism may be configured for applying the single mechanical energy input to the drive assembly to create the same moment on the first moment arm and the second moment arm respectively about a first axis and a second axis, such that the first moment arm applies a first one of the tensile outputs to the proximal end of the first pull wire, and the second moment arm applies a second one of the tensile outputs to the proximal end of the second pull wire, in accordance with the preset pull wire tension ratio. The first moment arm and the second moment arm may have different lengths, such that the first tensile output and second tensile output are different.

In one embodiment, the first axis and the second axis may be common, in which case, the drive assembly may comprise a pulley including an axle to which the control mechanism is configured for applying the mechanical energy input, and a wheel around which the proximal end of the first pull wire is looped, and the mechanical transmission linkage comprises a lever having lever arm and a hinge corresponding to the common axis. The drive assembly may further comprise a yoke having two arms, the axle of the pulley being may be rotatably affixed between the two arms of the yoke, and the control mechanism may be coupled to the yoke for applying the mechanical energy input to the axle of the pulley.

In this embodiment, the proximal end of the first pull wire is engaged to the lever arm at a first anchor point to create the first moment arm, and the proximal end of the second pull wire is engaged to the lever arm at a second anchor point to create the second moment arm. The first anchor point may be located between the second anchor point and the hinge, such that the preset pull wire tension ratio of the first tensile output over the second tensile output is greater than unity. The proximal end of the first pull wire may be slidably engaged to the lever arm, such that the first anchor point is adjustable along a length of the lever arm to adjust the length of the first moment arm, and thus, the preset pull wire tension ratio of the first tensile output over the second tensile output.

In this embodiment, the intravascular device may further comprise a wire tension ratio adjustment mechanism configured for adjusting the first anchor point along the length of the lever arm. For example, the wire tension ratio adjustment mechanism may comprise a slider carriage to which the proximal end of the first pull wire is affixed. The slider carriage may be configured for being displaced along the lever arm to adjust the first anchor point along the length of the lever arm. The lever arm may have a lengthwise slot and the slider carriage may have a protuberance to which the proximal end of the first pull wire is affixed. The protuberance may be configured for slidably engaging the slot of the lever arm. The slider carriage may comprise first and second collars transversely straddling the lever arm, and the wire tension ratio adjustment mechanism may further comprise a first rod and a second rod respectively threadedly engaged in the first collar and the second collar of the slider carriage, a drive gear affixed to the first rod, and an idle gear affixed to the second rod. The drive gear and the idle gear may be engaged with each other, such that rotation of the first rod causes the second rod to rotate via the engagement between the drive gear and the idle gear, thereby displacing the slider carriage along the lever arm.

If one of the preset pull wire tension ratio and the preset pull wire displacement ratio comprises the preset pull wire displacement ratio, the mechanical energy outputs are linear displacement outputs. In this case, the mechanical transmission linkage may comprise a first cam to which a proximal end of a first one of the pull wires is operatively coupled, a second cam to which a proximal end of a first one of the pull wires is operatively coupled, and a drive assembly operatively coupled to the first cam and the second cam. The control mechanism may be configured for applying the mechanical energy input to the drive assembly, such that the first cam applies a first one of the linear displacement outputs to the proximal end of the first pull wire, and the second cam applies a second one of the linear displacement outputs to the proximal end of the second pull wire, in accordance with the preset pull wire displacement ratio.

The first cam may comprise a first linear element to which the proximal end of the first pull wire is affixed, the first cam may comprise a first rotary element engaged with the drive assembly, and the second cam may comprise a second linear element to which the proximal end of the second pull wire is affixed, and a second rotary element engaged with the drive assembly. The control mechanism may be configured for applying the mechanical energy input to the drive assembly, such that the first rotary element and the second rotary element have the same angular displacement, and the first rotary element and the second rotary element may have different radii, such that the first linear displacement output and second linear displacement output are different.

In one embodiment, the drive assembly may comprise a linear drive rack having a first geared side and a second geared side opposite the first geared side, the first linear element may comprise a first linear gear affixed to the proximal end of the first pull wire, the first rotary element may comprise a first rotary gear and a second rotary gear fixed in relation to the first rotary gear, the first rotary gear may be engaged with the first linear gear, the second rotary gear may be engaged with the first geared side of the linear drive rack, the second linear element may comprise a second linear gear affixed to the proximal end of the second pull wire, the second rotary element may comprise a third rotary gear engaged between the second linear gear and the second geared side of the linear drive rack, and the control mechanism may be configured for applying the mechanical energy input to the linear drive rack, such that the first rotary gear and the second rotary gear rotate in unison to linearly displace the first linear gear, thereby applying the first tensile output to the proximal end of the first pull wire, and the third rotary gear rotates to linear displace the second linear gear, thereby applying the second tensile output to the proximal end of the second pull wire, in accordance with the preset pull wire displacement ratio. The radius of the first rotary gear may be different from a radius of the third rotary gear, such that the preset pull wire displacement ratio is different from unity.

In another embodiment, the drive assembly comprises an axle, the first linear element comprises a first belt, the second linear element comprises a second belt, the mechanical transmission linkage comprises a wheel assembly having a first annular groove that forms the first rotary element, and a second annular groove that forms the second rotary element. The first belt is looped around the first annular groove of the wheel assembly to form a first distal end coupled to the proximal end of the first pull wire and a second distal end coupled to a first anchor point, the second belt is looped around the second annular groove of the wheel assembly to form a first distal end coupled to the proximal end of the second pull wire and a second distal end coupled to a second anchor point, and the control mechanism is configured for applying the linear input force to the axle, such that first annular groove rotates to linearly displace the first belt, thereby applying the first linear displacement output to the proximal end of the first pull wire, and the second annular groove rotates to linearly displace the second belt, thereby applying the second linear displacement output to the proximal end of the second pull wire, in accordance with the preset pull wire displacement ratio. The looped belt may have a first radius, and the second looped belt may have second radius different from the first radius, such that the preset pull wire displacement ratio is different from unity.

In this embodiment, the first looped belt has a first radius, and the second looped belt has a second radius, and the intravascular device further comprises a pull wire displacement ratio adjustment mechanism configured adjusting at least one of the first radius of the first looped belt and the second radius of the second looped belt. The wheel assembly may comprise first and second outer plates disposed on the axle. The first and second outer plates are laterally affixed along the axle and respectively having convex conical surfaces that face each other. The wheel assembly may further comprise an inner plate slidably disposed along the axle between the first and second outer plates. The drive assembly may further comprise a yoke having two arms, the axle may be rotatably affixed between the two arms of the yoke, and the control mechanism may be coupled to the yoke for applying the mechanical energy input to the axle of the pulley.

The inner plate may have opposing first and second convex conical surfaces that respectively face the convex conical surfaces of the first and second outer plates, whereby the first annular groove is formed between the convex conical surface of the first outer plate and the first convex conical surface of the inner plate. The second annular groove may be formed between the convex conical surface of the second outer plate and the second convex conical surface of the inner plate. The first belt may have inwardly angled opposing surfaces that respectively conform to the convex conical surface of the first outer plate and the first convex conical surface of the inner plate, thereby setting a first radius of the first looped belt, and the second belt may have inwardly angled opposing surfaces that respectively conform to the convex conical surface of the second outer plate and the second convex conical surface of the inner plate, thereby setting a second radius of the second looped belt. The intravascular device may further comprise a pull wire displacement ratio adjustment mechanism configured for laterally sliding the inner plate along the axle, whereby a width of the first annular groove is increased, thereby decreasing the radius of the first looped belt, such that the first tensile output decreases, while a width of the second annular groove is decreased, thereby increasing the radius of the second looped belt, such that the second tensile output increases, whereby the preset pull wire displacement ratio is modified. Each of the first and second belts may have a trapezoidal cross-section.

The pull wire displacement ratio adjustment mechanism may comprise a slider carriage configured for being laterally displaced along a direction of the axle. The sider carriage may have a groove in which an outer portion of the inner plate is disposed, such that displacement of the slider carriage slides the inner plate along the axle. The pull wire displacement ratio adjustment mechanism may further comprise a pair of rails extending in a direction along the axle. The slider carriage may be configured for sliding along the pair of rails.

In still another embodiment, the first rotary element and the second rotary element may have the same radii, and the control mechanism may be configured for applying the mechanical energy input to the drive assembly, such that the first rotary element and the second rotary element have different angular displacements, whereby the first linear displacement output and second linear displacement output are different. The assembly may comprise a first cone, a second cone inversely oriented with respect to, and rotatably engaged with, the first cone, and a belt frictionally disposed between the first cone and the second cone. The first rotary element may comprise a first rotary gear affixed adjacent to a base of the first cone, and the second rotary element may comprise a second rotary element comprises a second rotary gear affixed adjacent to a base of the second cone. The first linear element may comprise a first linear gear operatively engaged with the first rotary gear, the first linear gear may be affixed to the proximal end of the first pull wire, the second linear element may comprise a second linear gear operatively engaged with the second rotary gear, and the second linear gear may be affixed to the proximal end of the second pull wire. The control mechanism may be configured for applying the mechanical energy input to the belt, such that first cone and the first rotary gear rotate in unison to linearly displace the first linear gear, thereby applying the first linear displacement output to the proximal end of the first pull wire, and the second cone and the second rotary gear rotate in unison to linearly displace the second linear gear, thereby applying the second linear displacement output to the proximal end of the second pull wire, in accordance with the preset pull wire displacement ratio.

The belt may be frictionally disposed between the first cone and the second cone at a first location coincident with a first radius of the first cone and a second radius of the second cone different from the first cone, such that the preset pull wire displacement ratio is different from unity. The belt may be configured for being laterally displaced between the first cone and the second cone. The intravascular device may further comprise a pull wire displacement ratio adjustment mechanism configured for laterally displacing the belt between the first cone and the second cone. The pull wire displacement ratio adjustment mechanism may comprise a pivotable carriage comprising a plurality of arms configured for supporting the belt along the length of the belt, and a pivot arm extending along the length of the belt, and around which the plurality of arms pivot to laterally displace the belt between the first cone and the second cone. The drive assembly may further comprise a slider configured for sliding along an axis parallel to the pivot arm of the pivotable carriage. The control mechanism may be coupled to the yoke for applying the mechanical energy input to the slider. The slider may have a guide slot along which a proximal end of the belt is slidably engaged. The guide slot may have an angle corresponding to an angle of the interface between the first cone and the second cone, such that proximal end of the belt slides along the guide slot when the belt is laterally displaced between the first cone and the second cone.

In some embodiments, the energy transmission linkage may be a fluidic energy transmission linkage, and the single energy input may be a single mechanical energy input. In this case, the energy transmission conduits may be mechanical energy transmission conduits, and the energy outputs may be mechanical energy outputs. Alternatively, the energy transmission conduits may be fluidic energy transmission conduits, and the energy outputs may be fluidic energy outputs.

Other and further aspects and features of embodiments will become apparent from the ensuing detailed description in view of the accompanying figures.

BRIEF DESCRIPTION OF THE DRAWINGS

The drawings illustrate the design and utility of preferred embodiments of the disclosed inventions, in which similar elements are referred to by common reference numerals. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. Further, an aspect or an advantage described in conjunction with a particular embodiment of the disclosed inventions is not necessarily limited to that embodiment and can be practiced in any other embodiments even if not so illustrated.

In order to better appreciate how the above-recited and other advantages and objects of the disclosed inventions are obtained, a more particular description of the disclosed inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 2A-2C are plan views of the catheter of FIG. 1A transitioning from a straight configuration to a curve configuration;

FIGS. 3A-3C are plan views of a prior art catheter transitioning from a straight configuration to a curve configuration;

FIG. 4A is a plan view of one embodiment of an elongated catheter body of the catheter of FIG. 1A, particularly showing the distal end of the catheter body in a straight configuration;

FIG. 4B is a plan view of the elongated catheter body of FIG. 4A, particularly showing the distal end of the catheter body in a curved configuration in accordance with one preset control parameter ratio;

FIG. 4C is a partially cut-away cross-sectional view of the elongated catheter body of FIG. 4A, taken along the longitudinal axis of catheter body;

FIG. 5A is a plan view of the elongated catheter body of FIG. 4A, particularly showing the distal end of the catheter body in a curved configuration in accordance with another preset control parameter ratio;

FIG. 5B is a plan view of the elongated catheter body of FIG. 4A, particularly showing the distal end of the catheter body in a curved configuration in accordance with still another preset control parameter ratio;

FIG. 6A is a plan view of a handle with one embodiment of a control mechanism and mechanical energy linkage of the catheter of FIG. 1A;

FIG. 6B is a cross-sectional view of the handle, control mechanism, and mechanical energy linkage of FIG. 6A;

FIG. 15 is a front view of a camming assembly used by the mechanical transmission linkage of FIG. 11;

FIG. 16 is a side view of a camming assembly used by the mechanical transmission linkage of FIG. 11;

FIG. 20 is a top view of the mechanical transmission linkage of FIG. 18;

FIG. 21 is a side view of the mechanical transmission linkage of FIG. 18;

DETAILED DESCRIPTION OF THE ILLUSTRATED EMBODIMENTS

Figure 1A:
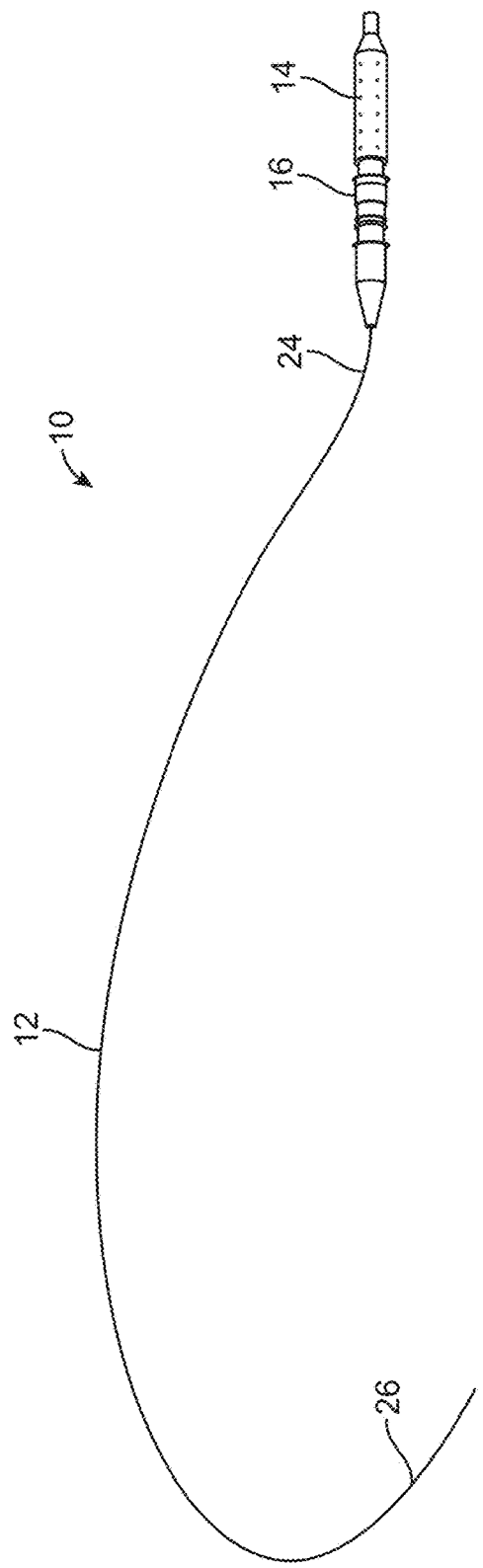
FIG. 1A is a plan view of catheter constructed in accordance with one embodiment of the disclosed inventions, particularly showing a distal end of the catheter in a straight configuration.
Figure 1B:
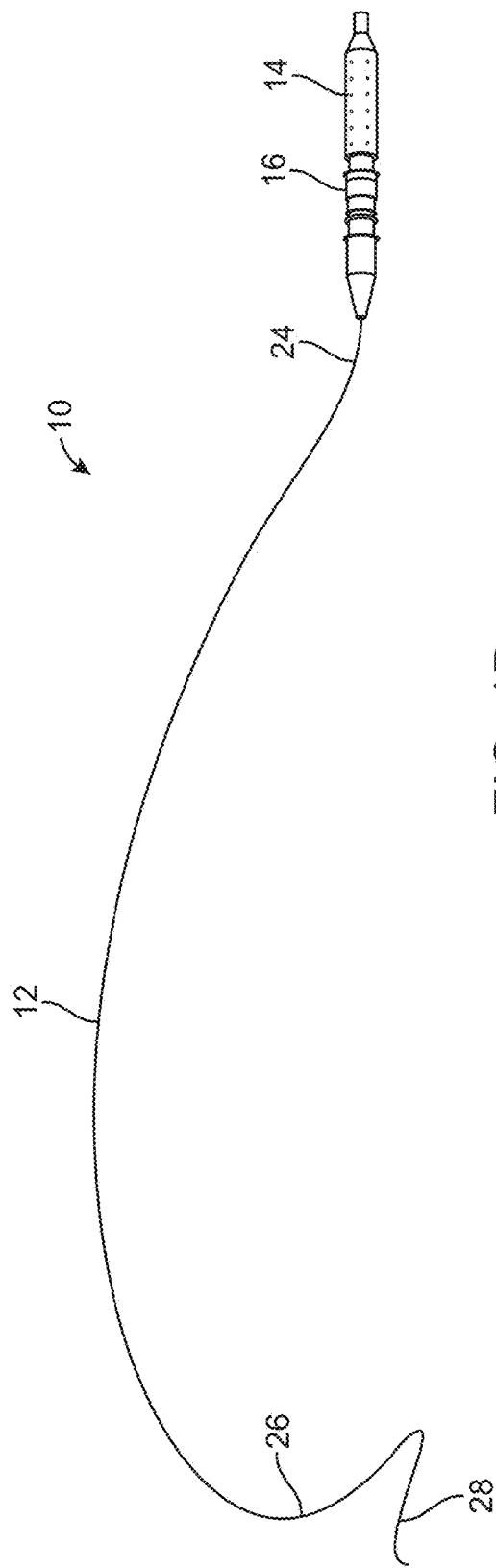
FIG. 1B is a plan view of the catheter of FIG. 1A, particularly showing the distal end of the catheter in a curved configuration.

Referring to FIGS. 1A and 1B, one embodiment of a deflectable elongated intravascular device 10 constructed in accordance with one embodiment of the present inventions will now be described. In the illustrated embodiment, the deflectable elongated intravascular device 10 is described as a guide catheter configured for guiding working catheters (e.g., a therapeutic or diagnostic catheter) or other instruments to a target site within the body of a patient, although it should be appreciated that the elongated intravascular device 10 can take the form of any device, including a selective catheter, guidewire, or even the working catheter, itself, that is purposed to perform a medical procedure that can benefit from the use of compound curves.

The deflectable catheter 10 generally comprises an elongated catheter body 12 having a proximal end 24 and a distal end 26, a handle 14 affixed to the proximal end 24 of the catheter body 12, and a control mechanism 16 associated with the handle 12. The distal end 26 of the catheter body 12 is configured for selectively transforming between a straight configuration (FIG. 1A) and a curved configuration (FIG. 1B) in response manual manipulation of the control mechanism 12 associated with the handle 14, as will be described in further detail below.

The handle 14 is configured for being manually grasped by an operator, and may be composed of a durable and rigid material, such as medical grade plastic, and ergonomically molded to allow an operator to more easily manipulate the deflectable catheter 10. The curved configuration is characterized by a compound curve 28 (i.e., a curve having multiple different bends either in-plane or out-of-plane with respect to each other). In an alternative case where the distal end 26 of the catheter body 12 may assume multiple compound curves, multiple control mechanisms 16 may be provided (i.e., one control mechanism 16 associated with each compound curve). Furthermore, although the distal end 26 of the catheter body 12 assumes the compound curve 28 in response to manual manipulation of a control mechanism 16 located on a handle 14, it should be appreciated that the distal end of the catheter body in alternative embodiments of the deflectable catheter 10 may assume a compound curve in response to automated manipulation of a control mechanism associated with a proximal adapter, e.g., by an automated drive unit to which the proximal adapter couples.

Significantly, the distal end 26 of the catheter body 12 is configured for assuming the compound curve 28 in response to a single action manipulation of the control mechanism 16 by the operator, thereby providing a simpler and more robust means for creating the compound curve 28. This single action manipulation feature is enabled by the use of an energy transmission linkage 18 (see FIGS. 6A and 6B) operably coupled between the control mechanism 16 and a plurality of energy transmission conduits 20 extending through the catheter body 12 (see FIG. 4C) and terminating at different axial locations along the distal end 26 thereof. In the illustrated embodiment, the total number of energy transmission conduits 20 is two (20a and 20b), although any plural number of energy transmission conduits 20 may be used. As a general rule, the total number of bends in the compound curve 28 or compound curves that the distal end 26 of the deflectable catheter 10 assumes will equal the minimum number of energy transmission conduits 20. Thus, if the compound curve consists of more than two bends or if distal end 26 of the catheter body 12 is to assume multiple compound curves, more than two energy transmission conduits 20 are generally employed.

As will be described in further detail below, the energy transmission linkage 18 is configured for, in response to a single energy input applied to the energy transmission linkage 18 by the control mechanism 16, simultaneously applying a plurality of energy outputs respectively to the proximal ends of the energy transmitting conduits 20a, 20b at a preset control parameter ratio. The preset control parameter ratio can be any ratio between values of a parameter that respectively affect the bends of a compound curve (i.e., a first value of the parameter affects a first bend of the compound curve, a second value of the same parameter affects a second bend of the compound curve, etc.). The parameter can be an output of the energy transmission linkage 18, e.g., force, linear displacement, volume, pressure, amperage, voltage, lumens, etc., or can be internal to the energy transmission linkage 18, e.g., a length of moment arm, piston area, pulley radius, gear radius, screw pitch etc.).

As will also be described in further detail below, in some embodiments of the deflectable catheter 10, the final shape of the compound curve 28 assumed by the distal end 26 of the catheter body 12 can be adjustable (continuously or discretely) via a control parameter ratio adjustment mechanism 22 configured for adjusting the preset control parameter ratio of the energy transmission linkage 18.

Referring now to FIGS. 2A-2C, the gradual transformation of the distal end 26 of the catheter body 12 of the deflectable catheter 10 from a straight configuration to the curved configuration consisting of the compound curve 28 will be described. In the illustrated embodiment, the compound curve 28 that the distal end 26 of the catheter body 12 assumes a 90-degree proximal bend 30 away from a longitudinal axis 34 of the catheter body 12, followed by a 180-degree distal bend 32 back towards the longitudinal axis 34 of the catheter body 12, with the proximal bend 30 and distal bend 32 disposed in the same plane. It should be appreciated that the compound curve illustrated in FIG. 2C is only exemplary, and alternative embodiments of the deflectable catheter 10 may comprise different types of compound curves having different shapes or different numbers of bends, including bends that are out-of-plane with each other, or even multiple compound curves.

As illustrated in FIG. 2A, the distal end 26 of the catheter body 12 is in a straight configuration. In response to a single action manipulation of the control mechanism 16 associated with the handle 14 of the deflectable catheter 10, the distal end 26 of the catheter body 12 begins to partially assume a compound curve 28' that has a partially formed proximal bend 30' and a partially formed distal bend 32' that are simultaneously articulated, as illustrated in FIG. 2B. In response to further single action manipulation of the control mechanism 16, the distal end 26 of the catheter body 26 fully assumes the compound curve 28 that has a completely formed proximal bend 30 (i.e., a 90-degree bend) and a completely formed distal bend 32 (i.e., a 180-degree bend) that are simultaneously articulated, as illustrated in FIG. 2C.

The single action manipulation feature of the deflectable catheter 10 should be contrasted with prior art deflectable catheters that progressively form a compound curve using multiple independently controllable mechanism that require the operator to tediously balance articulation of the multiple bends of the compound curve. For example, referring now to FIGS. 3A-3C, the gradual transformation of a distal end 3 of a catheter body 2 of a prior art deflectable catheter 1 from a straight configuration to the curved configuration consisting of a compound curve 4 analogous to the compound curve 28 of the deflectable catheter 10 will be described. As illustrated in FIG. 3A, the distal end 3 of the catheter body 2 is in a straight configuration similar to the distal end 26 of the catheter body 12 of the deflectable catheter 10 illustrated in FIG. 2A. The operator must first actuate one of the control mechanisms (not shown) to form the distal bend 6 of the compound curve 4 in the distal end 3 of the catheter body 2, as illustrated in FIG. 3B, and then actuate the other control mechanism (not shown) to form the proximal bend 5 of the compound curve 4 in the distal end 3 of the catheter body 2, as illustrated in FIG. 3C. Although the prior art deflectable catheter 1 illustrated in FIGS. 3A-3C can ultimately achieve the same compound curve as the deflectable catheter 10 illustrated in FIGS. 2A-2C, multiple steps are required to form the compound curve with the prior art deflectable catheter 1. Furthermore, since the formation of the proximal bend 5 may affect the distal bend 6, the operator may need to iteratively form the distal bend 6 and proximal bend 5 in order to achieve the proper shape in the compound curve. As such, the prior art deflectable catheter 1 may not be as user friendly as the deflectable catheter 10 when creating the compound curve.

Having generally described the arrangement and functioning of the deflectable catheter 10, the catheter body 12, handle 14, control mechanism 16, energy transmission linkage 18, and energy transmission conduits 20a, 20b will now be described in further detail.

Referring first to FIGS. 4A-4C, the catheter body 12 of the deflectable catheter 10 is substantially pliable or flexible, such that when it is advanced into a patient, the catheter body 12 will conform, adopt, or match the shape or curvatures of the internal pathways (e.g., gastrointestinal tract, blood vessels, etc.) of the patient. Alternatively, the catheter body 12 may be semi-rigid, i.e., by being made of a stiff material, or by being reinforced with a coating or coil, to limit the amount of flexing. The catheter body 12 is preferably about 2 French to 9 French in diameter, and between 80 cm to 150 cm in length. The catheter body 12 preferably has a cross-sectional geometry that is circular. However, other cross-sectional shapes, such as elliptical, rectangular, triangular, and various customized shapes, may be used as well. The catheter body 12 is preferably preformed of an inert, resilient plastic material that retains its shape and does not soften significantly at body temperature; for example, Pebax®, polyethylene, polyurethane, polyamide or Hytrel® (polyester). Alternatively, the catheter body 12 may be made of a variety of materials, including, but not limited to, metals and polymers. The catheter body 12 is preferably flexible so that it is capable of winding through a tortuous path that leads to a target site, i.e., an area within the heart. The catheter body 12 may be composed of multiple layers of materials and/or multiple tube structures that exhibit a low bending stiffness, while providing a high axial stiffness along the longitudinal axis of the catheter body 12. Typical designs include a nitinol spine encapsulated in braid and any flexible, pliable, or suitable polymer material or bio-compatible polymer material or a braided plastic composite structure composed of low durometer plastics (e.g., nylon-12, Pebax®, polyurethanes, polyethylenes, etc.).

In this embodiment, the catheter body 12 is functionally divided into four sections: an atraumatic distal tip 34, a distal articulating section 36, an intermediate transition section 38, and a proximal shaft section 40.

The atraumatic distal tip 34 is rounded and includes an exit port (not shown) in communication with a central working lumen 42 (shown in FIG. 4C) and from which a working catheter or guidewire may extend distally therefrom. The atraumatic tip 34 may be composed of a suitable polymer material (e.g., Pebax®).

The distal articulating section 36 preferably allows for a moderate degree of axial compression and optimal lateral flexibility. The distal articulating section 36 has a several portions of differing rigidities formed by having different outer tubes composed of a suitable polymer material (e.g., Pebax®). In the illustrated embodiment, the distal articulating section 36 comprises a relatively flexible proximal segment 36a, which is designed to articulate to form the proximal bend 30 of the compound curve 28 (as best shown in FIG. 4B), a relatively rigid proximal segment 36b abutting the relatively flexible proximal segment 36a, a relatively flexible distal segment 36c, which is designed to articulate to form the distal bend 32 of the compound curve 28, abutting the relatively rigid proximal segment 36b, and a relatively rigid distal segment 36d abutting the relatively flexible distal segment 36c. The length of the distal articulating section 36 can vary depending on the performance requirements for the deflectable catheter 10. A longer distal articulating section 36 may be beneficial to increase the area of reach, while a shorter distal articulating section 36 may be beneficial for cannulating tight side branches in the anatomical vasculature. To increase its axial rigidity and elastic properties, the distal articulating section 36 may comprise a braided layer (e.g., sixteen 0.0005"×0.003" spring temper 304V stainless steel wires braided at 68 picks per inch (ppi) in a 2 over 2 pattern) embedded within the outer polymer tubes, may comprise a coil with a varied pitch, or may comprise a slotted (e.g., micromachined) hypotube to tailors the flexibility and bending plane of the distal articulating section 36.

The intermediate transition section 38 resists axial compression to clearly define the proximal end of the distal articulating section 36 and transfer the motion of the energy transmission conduits 20a, 20b to the distal articulating section 36, while maintaining lateral flexibility to allow the deflection catheter 10 to track over tortuous anatomies. The intermediate transition section 38 may be formed of an outer tube composed of a suitable polymer material (e.g., Pebax®).

The proximal shaft section 40 gradually transitions the catheter body 12 from the intermediate transition section 38 to the more rigid remaining portion of the catheter body 12 by having several portions of differing rigidities formed by having different outer tubes composed of a suitable polymer material (e.g., Pebax®). To increase its axial rigidity, the proximal shaft section 10 may comprise a double braided layer (e.g., sixteen 0.0005"×0.003" spring temper 304V stainless steel wires braided at 68 picks per inch (ppi) in a 2 over 2 pattern) embedded within the outer polymer tubes.

As best shown in FIG. 4C, the central working lumen 42 is disposed through the entire length of the catheter body 12 for delivering a working catheter (not shown) or one or more instruments or tools from the proximal end 24 of the catheter body 12 to the distal end 26 of the catheter body 12. The nature of the working lumen 42 will depend on the intended use of the deflectable catheter 10. For example, in the illustrated embodiment, the deflectable catheter 10 is to be used as a guide sheath, in which case, the working lumen 42 will serve to accommodate a working catheter or other instrument). If the deflectable catheter 10 is to be used as a working or selective catheter, the working lumen 42 will serve to accommodate a guide wire (not shown). At least a portion of the working lumen 42 extending through the catheter body 12 may be formed by an inner polymer tube (e.g., 0.001" thick polytetrafluoroethylene (PTFE)).

In the illustrated embodiment, the energy transmission conduits 20a, 20b are mechanical energy transmission conduits, and in particular, take the form of pull wires that extend within the elongated catheter body 14. Each of pull wires 20a, 20b may be a metallic wire, cable or filament, or it may be a polymeric wire, cable or filament. Each pull wire 20a, 20b may also be made of natural or organic materials or fibers. Each pull wire 20a, 20b may be any type of suitable wire, cable or filament capable of supporting various kinds of loads without deformation, significant deformation, or breakage. Although mechanical energy transmission conduits have been described as being pull wires 20a, 20b, it should be appreciated that the mechanical energy transmission conduits should not be limited to pull wires. For example, the mechanical transmission conduits 20a, 20b may take the form of small diameter tubes or rods that are axially rigid, but laterally flexible. Furthermore, in alternative embodiments of the deflectable catheter 10, non-mechanical, e.g., fluid transmission conduits (e.g., hydraulic or pneumatic), electrical transmission conduits (i.e., electrical wires), electromagnetic energy (e.g., optical) transmission conduits, etc., may be used as energy transmission conduits. Essentially, any energy transmission conduit capable of transmitting any energy from the proximal end 24 to the distal end 26 of the catheter body 12 for articulating the distal articulating section 36 into the compound curve 28 may be used.

In order to impart different forces along the distal end 26 of the elongated catheter body 12 to create the compound curve 28, the pull wires 20a, 20b are slidably disposed within one or more pull wire lumens 44 extending through the catheter body 12, as best shown in FIG. 4C. The pull wire lumens 44 may be constructed of a low friction material or may simply be unsupported tubular cavities in which the pull wires 20a, 20b respectively float. In the illustrated embodiment, the two pull wire lumens 44a, 44b are provided in the catheter body 12 in a 180-degree circumferentially spaced apart relationship. In the alternative embodiment where more than two pull wires 20a, 20b are used, additional pull wire lumens 44 can be provided in the catheter body 12. In the illustrated embodiment, the pull wire lumens 44 extend proximally from the distal articulating section 36 through the proximal shaft section 40. In alternative embodiments, the intermediate transition section 38 may transition the two pull wire lumens 44a, 44b in the distal articulating section 36 to a single hollow stiffening tube (not shown) extending through the proximal shaft section 40.

The proximal ends of the pull wires 20a, 20b are operatively coupled to the control mechanism 16 via the energy transmission linkage 18 (shown in FIGS. 6A and 6B), while the distal ends of the pull wires 20a, 20b are respectively affixed to the distal end 26 of the catheter body 12 at different axial locations, such that operation of the pull wires 20a, 20b via manual actuation of the control mechanism 16 applies or modifies a force or tension to distal end 26 of the catheter body 12 at the different axial locations, which may steer or articulate (e.g., up, down, pitch, yaw, or any direction in-between) portions of the distal end 26 of the catheter body 12 in the direction of the pull wires 20*a*, 20*b* to create the compound curve 28. The control mechanism 16 comprises springs (not shown) that pre-tension the pull wires 20*a*, 20*b*, such that the pull wires 20*a*, 20*b* are always under tension. Thus, the control mechanism 16 serves to increase or decrease the tension on the pull wires 20*a*, 20*b* to proximally or distally displace the pull wires 20*a*, 20*b* within the respective pull wire lumens 44*a*, 44*b*.

In the illustrated embodiment, the distal end of one pull wire 20*a* is affixed to the distal end 26 of the catheter body 12 at the distal extent of the relatively flexible proximal segment 36*a* of the distal articulating section 36, such that increased tension on the pull wire 20*a* articulates the relatively flexible proximal segment 36*a* into the proximal bend 30 of the compound curve 28, while the distal end of the other pull wire 20*b* is affixed to the distal end 26 of the catheter body 12 at the distal extent of the relatively flexible distal segment 36*c* of the distal articulating section 36, such that increased tension on the pull wire 20*b* articulates the relatively flexible distal segment 36*c* into the distal bend 32 of the compound curve 28. In the illustrated embodiment, the distal articulating section 36 of the deflectable catheter 10 is resilient, such that releasing the pull wires 20*a*, 20*b* via manual actuation of the control mechanism 16 will release the internal force or tension on the distal articulating section 36, allowing it to return to a straight configuration.

To facilitate affixation of the pull wires 20*a*, 20*b* to the distal end 26 of the distal articulating section 36, the deflectable catheter 10 further includes a plurality of control rings 46 (shown in phantom), and in this case a proximal control ring 46*a* and a distal control ring 46*b* (one for each pull wire 20*a*, 20*b*), secured around the working lumen 42 at different axial locations along the distal end 26 of the catheter body 12. The distal ends of the pull wires 20*a*, 20*b* are respectively anchored or mounted to the control rings 46*a*, 46*b*, such that operation of the pull wires 20*a*, 20*b* via manual actuation of the control mechanism 16 applies a force or tension to the control rings 46*a*, 46*b*, thereby articulating the distal end 26 of the catheter body 12. In the illustrated embodiment, the proximal control ring 46*a* is located between the relatively flexible proximal segment 36*a* and the relatively rigid proximal segment 36*b* of the distal articulating section 36, and the distal control ring 46*b* is located between the relatively flexible distal segment 36*c* and the relatively rigid distal segment 36*d* of the distal articulating section 36. The distal ends of the pull wires 20*a*, 20*b* are respectively affixed to locations of the control rings 38*a*, 38*b* that are circumferentially spaced apart by 180 degrees, such that the proximal bend 30 and distal end 32 of the compound curve 28 are disposed in the same plane in response to tensioning of the pull wires 20*a*, 20*b*. Alternatively, the distal ends of the pull wires 20*a*, 20*b* may be respectively affixed to locations of the control rings 38*a*, 38*b* that are circumferentially spaced apart by an amount different than 180 degrees (e.g., 90 degrees), such that the proximal bend 30 and distal end 32 of the compound curve 28 are disposed in different planes in response to tensioning of the pull wires 20*a*, 20*b*.

In alternative embodiments, no control rings are used in the deflectable catheter 10. Instead, the distal ends of the pull wires 20*a*, 20*b* may be attached directly to a section or portion of the catheter body 12 (e.g., directly anchored between the two layers of the braid), where it may be steered, articulated, or bent. The pull wires 20*a*, 20*b* may be crimped, soldered, welded or interlocked in any suitable manner to specific locations along the distal end 26 of the catheter body 12, and in this embodiment, at one location between the relatively flexible proximal segment 36*a* and the relatively rigid proximal segment 36*b* of the distal articulating section 36, and at the other location between the relatively flexible distal segment 36*c* and the relatively rigid distal segment 36*d* of the distal articulating section 36.

In the illustrated embodiment, the energy transmission linkage 18 is a mechanical energy transmission linkage operably coupled between the proximal ends of the mechanical energy transmission conduits 20*a*, 20*b* (and in this case, the two pull wires 20*a*, 20*b*) and the control mechanism 16 (or alternatively the drive unit in the case where the compound curve is formed automatically in the distal end 26 of the elongated catheter body 12), and the control mechanism 16 is configured for applying a single mechanical energy input to the mechanical energy transmission linkage 18. In this case, the mechanical energy transmission linkage 18 is configured for, in response to the single mechanical energy input applied by the control mechanism 16, simultaneously applying a plurality of the mechanical energy outputs respectively to the proximal ends of the mechanical energy transmitting conduits 20*a*, 20*b* at the preset control parameter ratio. Tensioning elements (e.g., springs) may be incorporated into the control mechanism 16 and/or mechanical transmission linkage 18, such that the pull wires 20*a*, 20*b* are constantly tensioned, and thus, actuation of the control mechanism 16 serves to increase or decrease the tensions on the pull wires 20*a*, 20*b*. Further details discussing various embodiments of the mechanical transmission linkage 18 will be set forth below.

Since the mechanical energy transmission conduits 20*a*, 20*b* are two pull wires in the illustrated embodiment, the mechanical energy outputs are simultaneously applied by the mechanical energy transmission linkage 18 to the proximal ends of the pull wires 20*a*, 20*b* by applying tensile outputs or linear displacement outputs to the pull wires 20*a*, 20*b*. In this case, the preset control parameter ratio may take the form of a preset pull wire tension ratio (the ratio between the two tensile outputs applied to the proximal ends of the two pull wires 20*a*, 20*b* (i.e., pull wire tension outputs)) or a preset pull wire displacement ratio (in this case, the ratio between linear displacement outputs applied to the proximal ends of the two pull wires 20*a*, 20*b* (i.e., pull wire displacement outputs). Selection of either a preset pull wire tension ratio or a preset pull wire displacement ratio as the control parameter ratio may depend on the desired performance of the compound curve 28 assumed by the distal end 26 of the catheter body 12. For example, if it is desired that distal end 26 of the catheter body 12 consistently assume and maintain the compound curve 28 regardless of dynamic forces (e.g., external forces applied by surrounding tissue on the distal end 26 of the catheter body 12, internal forces applied by the catheter body 12 to the pull wires 20, or internal forces applied to the distal end 26 of the catheter body 12 during transmission of the working catheter or guidewire through the portion of the working lumen 42 adjacent the distal end 26 of the catheter body 12), then it may be desirable to select the preset pull wire displacement ratio as the control parameter ratio. In contrast, if it desirable to provide a degree of flexibility in the compound curve 28, such that the working catheter or guidewire can more easily be transmitted through the working lumen 42 adjacent the distal end 26 of the catheter body 12, then it may be desirable to select the preset pull wire tension ratio as the control parameter ratio.

In the alternative embodiment where the energy transmission conduits 20a, 20b are fluidic energy transmission conduits, the energy transmission linkage 18 may be a hydraulic/pneumatic energy transmission linkage configured for, in response to the single mechanical energy input applied by the control mechanism 16, simultaneously applying a plurality of fluidic energy outputs respectively to the proximal ends of the fluidic energy transmitting conduits at the preset control parameter ratio. In this case, the preset control parameter ratio may, e.g., be a preset volume ratio, preset pressure ratio, preset piston area ratio, etc. In the alternative embodiment wherein the energy transmission conduits 20a, 20b are electrical wires, the energy transmission linkage 18 may be an electrical energy transmission linkage configured for, in response to the single electrical energy input applied by the control mechanism 16, simultaneously applying a plurality of electrical energy outputs respectively to the proximal ends of the pull wires 20a, 20b at the preset control parameter ratio. In this case, the preset control parameter ratio may, e.g., be a preset amperage ratio, preset voltage ratio, etc.

As briefly discussed above, the optional control parameter ratio adjustment mechanism 22 (shown in FIGS. 6A and 6B) is configured for adjusting the preset control parameter ratio of the energy transmission linkage 18, such that the relative extent of the proximal bend 30 and distal bend 32 of the fully formed compound curve 28 assumed by the distal end 26 of the catheter body 12 can be set. For example, the values of a control parameter associated with the respective energy transmission conduits 20, and in the illustrated embodiment, the values of the pull wire tension or pull wire displacement associated with the pull wires 20a, 20b, can be adjusted by the control parameter ratio adjustment mechanism 22 to decrease the distal bend 32 of the fully formed compound curve 28 assumed by the distal end 26 of the catheter body 12.

For example, as shown in FIG. 5A, the extent of the distal bend 32 of the fully formed compound curve 28 has been decreased from 180 degrees to 135 degrees, while the extent of the proximal bend 30 remains unchanged at 90 degrees. In this case, the ratio of the tension or displacement of the pull wire 20a associated with the proximal bend 30 of the compound curve 28 over the tension or displacement of the pull wire 20b associated with the distal bend 32 of the compound curve 28 has been increased by the control parameter ratio adjustment mechanism 22 (e.g., from 1:2 to 2:3). Although the extent of the distal bend 32 of the fully formed compound curve 28 has been illustrated as being adjusted from 180 degrees to 135 degrees, the control parameter ratio adjustment mechanism 22 may be operated to adjust the distal bend 32 of the fully formed compound curve 28 to any angle, but generally less than 180 degrees, e.g., 160 degrees, 120 degrees, etc.

Figure 5C:
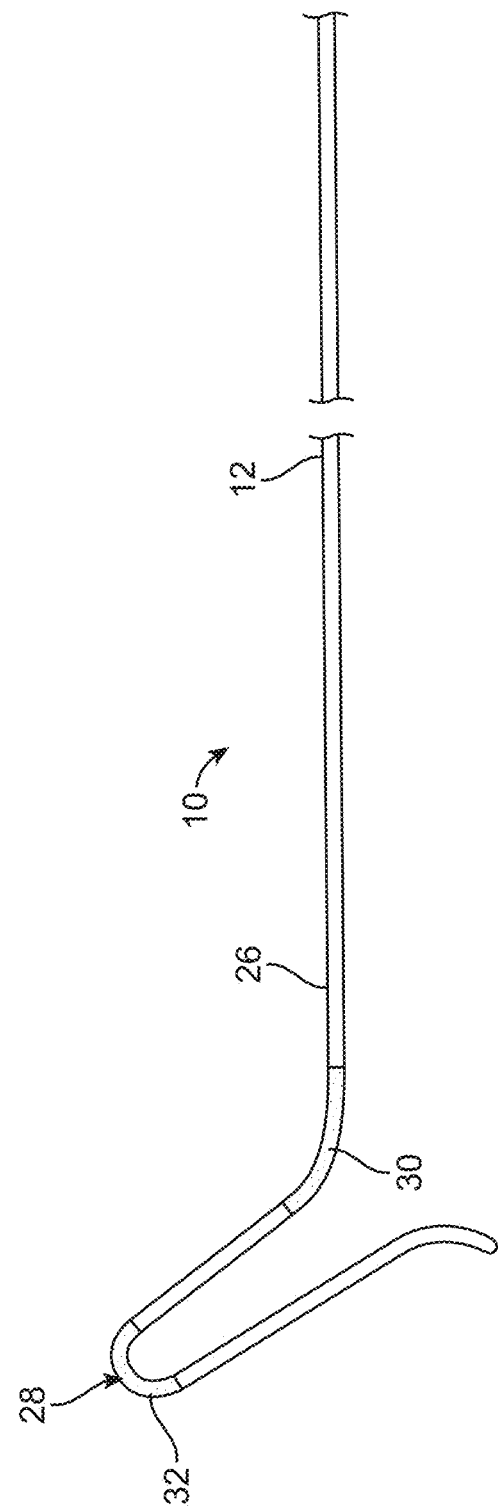
FIG. 5C is a plan view of the elongated catheter body of FIG. 4A, particularly showing the distal end of the catheter body in a curved configuration in accordance with yet another preset control parameter ratio.

As another example, as shown in FIG. 5B, the extent of the proximal bend 30 of the fully formed compound curve 28 has been increased from 90 degrees to 135 degrees, while the extent of the distal bend 32 remains unchanged at 180 degrees. In this case, the ratio of the tension or displacement of the pull wire 20a associated with the proximal bend 30 of the compound curve 28 over the tension or displacement of the pull wire 20b associated with the distal bend 32 of the compound curve 28 has been increased by the control parameter ratio adjustment mechanism 22 (e.g., from 1:2 to 2:3). As shown in FIG. 5C, the extent of the proximal bend 30 of the fully formed compound curve 28 has been increased from 90 degrees to 45 degrees, while the extent of the distal bend 32 remains unchanged at 180 degrees. In this case, the ratio of the tension or displacement of the pull wire 20a associated with the proximal bend 30 of the compound curve 28 over the tension or displacement of the pull wire 20b associated with the distal bend 32 of the compound curve 28 has been decreased by the control parameter ratio adjustment mechanism 22 (e.g., from 1:2 to 1:4).

As will be described in further detail below, the control parameter ratio adjustment mechanism 22 may comprise an external component, e.g., a dial, slider, lever, etc., that can be manipulated by an operator, and internal components that couple the external component of the control parameter ratio adjustment mechanism 22 to the energy transmission linkage 18.

Referring now to FIGS. 6A and 6B, the control mechanism 16 is configured for selectively providing a coarse adjustment and a fine adjustment of the tension on the pull wires 20a, 20b, and thus, providing a means of coarsely or finely adjusting the transformation of the distal end 26 of the catheter body 12 between the straight configuration and the curved configuration.

To this end, the control mechanism 16 comprises a collar sleeve 48 disposed about the handle 14 and a linear gear 50 slidably disposed within a cavity 52 of the handle 14. The collar sleeve 48 may be both linearly and rotationally displaced relative to the handle 14. The linear gear 50 is rotatably restrained by the handle 14, such that linear displacement of the linear gear 50 within the handle 14 constitutes the only freedom of movement of the linear gear 50 relative to the handle 14. The collar sleeve 48 comprises a threaded bore 54, and the linear gear 50 comprises a plurality of teeth 56 extending along the length of the linear gear 50. The control mechanism 16 further comprises a single pull wire 58, the proximal end of which is affixed to the linear gear 50, and the distal end of which is operably coupled to the pull wires 20a, 20b through the mechanical transmission linkage 18.

The threaded bore 54 of the collar sleeve 48 engages the teeth 56 of the linear gear 50, such that the threaded bore 44 of the collar sleeve 48 rides along the teeth 56 of the linear gear 50, thereby effecting fine (i.e., relatively minute) and continuous longitudinal translation of the linear gear 50 relative to the handle 14 in response to rotation of the collar sleeve 48 about the handle 14 in the clockwise or counter-clockwise direction. In particular, manual rotation of the collar sleeve 48 (as shown by the arrow 60) in one of a clockwise direction and a counterclockwise direction will finely translate the linear gear 50 in the proximal direction (shown by the arrow 62a). In turn, fine translation of the linear gear 50 proximally will finely displace the single pull wire 58 proximally in opposition to the spring force of the passive tensioning elements (not shown) in the handle 14 and resiliency of the catheter body 12, which in turn, will finely increase tension the pull wires 20a, 20b, thereby finely tightening the compound curve assumed by the distal end 26 of the catheter body 12. In contrast, manual rotation of the collar sleeve 48 in the other of the clockwise direction and a counterclockwise direction will finely translate the linear gear 50 in the distal direction (shown by the arrow 62b). In turn, fine translation of the linear gear 50 distally will allow spring force of the passive tensioning elements in the handle 14 and the resiliency of the distal end 26 of the catheter body 12 to finely translate the single pull wire 58 distally, which in turn, will finely relax the pull wires 20a, 20b, thereby finely allowing the distal end 26 of the catheter body 12 to return to its straight or relaxed configuration.

The threaded bore 54 of the collar sleeve 48 also engages the teeth 56 of the linear gear 50, such that the threaded bore 44 of the collar sleeve 48 is locked to the teeth 56 of the linear gear 50, thereby effecting coarse (i.e., relatively large) continuous longitudinal translation of the linear gear 50 relative to the handle 14 in response to linear displacement of the collar sleeve 48 relative to the handle 14. Linear displacement of the collar sleeve 48 in the proximal direction (shown by the arrow 64a) will coarsely translate the linear gear 50 in the proximal direction (shown by the arrow 62a). In turn, coarse translation of the linear gear 50 proximally will coarsely displace the single pull wire 58 proximally in opposition to the spring force of the passive tensioning elements (not shown) in the handle 14 and resiliency of the catheter body 12, which in turn, will coarsely increase tension on the pull wires 20a, 20b, thereby coarsely tightening the compound curve assumed by the distal end 26 of the catheter body 12. In contrast, linear displacement of the collar sleeve 48 in the distal direction (shown by the arrow 64b) will coarsely translate the linear gear 50 in the distal direction (shown by the arrow 62b). In turn, coarse translation of the linear gear 50 distally will allow spring force of the passive tensioning elements in the handle 14 and the resiliency of the distal end 26 of the catheter body 12 to coarsely translate the single pull wire 58 distally, which in turn, will coarsely relax the pull wires 20a, 20b, thereby coarsely allowing the distal end 26 of the catheter body 12 to return to its straight or relaxed configuration.

Although the control mechanism 16 has been described as being capable of both finely and coarsely placing the distal end 26 of the catheter body 12 between a straight configuration and a compound curve, it should be appreciated that in alternative embodiments, the control mechanism 16 may simply be capable of transforming the distal end 26 of the catheter body 12 between a straight or relaxed configuration and a compound curve without coarse or fine adjustments. Furthermore, in the case where the distal end 26 of the catheter body 12 can assume multiple compound curves, multiple control mechanisms 16 may be provided, such that the distal end 26 of the catheter body 12 may be transformed between any of the compound curves or between the compound curves and a straight relaxed configuration. For example, if the distal end 26 of the catheter body 12 is capable of assuming two compound curves, two control mechanisms can be provided, the first one of which can be coupled to two pull wires for transforming the distal end 26 of the catheter body 12 between a first compound curve and a second compound curve or straight or relaxed configuration, and the second one of which can be coupled to another two pull wires for independently transforming the distal end 26 of the catheter body 12 between the second compound curve and a first compound curve or straight or relaxed configuration.

Figure 7:
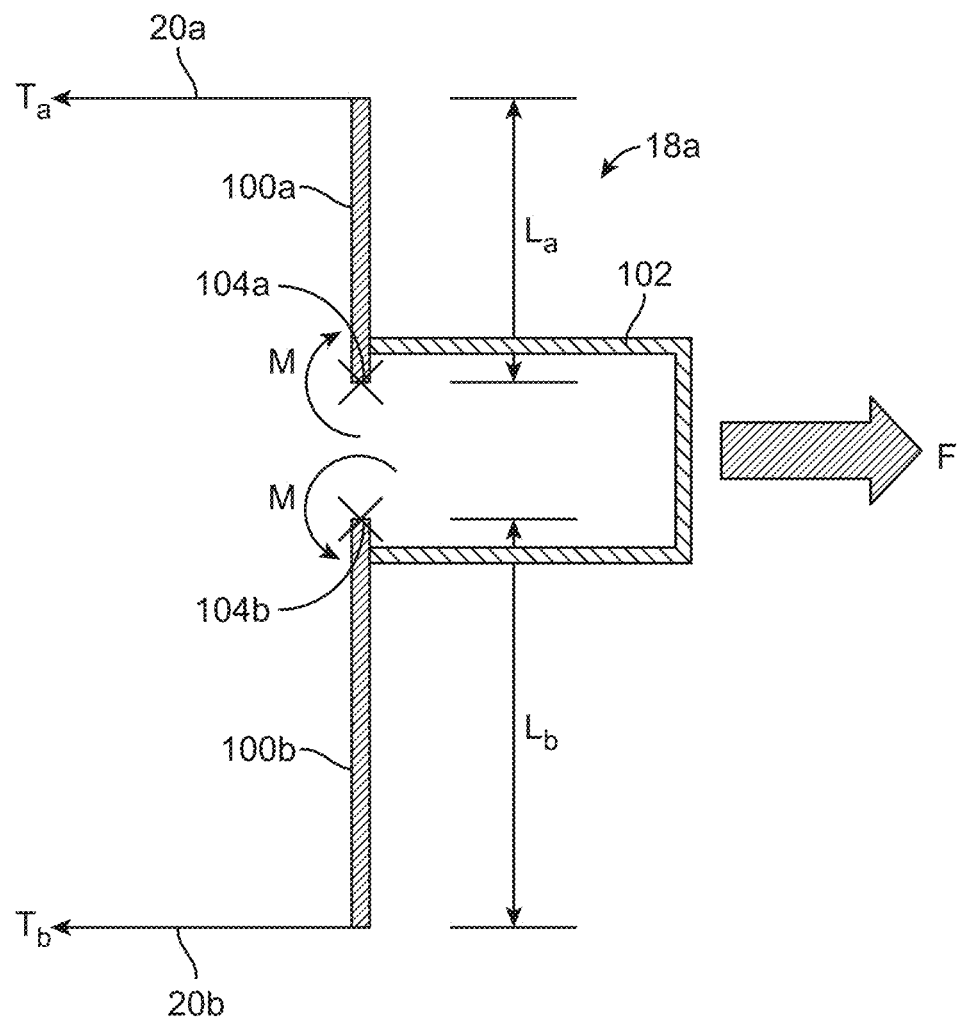
FIG. 7 is a plan view of one embodiment of a mechanical transmission linkage used in the catheter of FIG. 1A.

Referring now to FIG. 7, one exemplary embodiment of a mechanical energy transmission linkage 18a will be described. The mechanical energy transmission linkage 18a is configured for, in response to an input force F by the control mechanism 16 (shown in FIG. 1), simultaneously applying two tensile outputs $T_a$, $T_b$ respectively to the proximal ends of the two pull wires 20a, 20b in accordance with a preset pull wire tension ratio.

The mechanical energy transmission linkage 18a comprises a plurality of moment arms 100 to create a preset pull wire tension ratio between the pull wires 20, and in particular, a first moment arm 100a and a second moment arm 100b that respectively rotate about a first axis 104a and a second axis 104b to create a preset pull wire tension ratio between the two pull wires 20a, 20b. The moment arms 100a, 100b respectively have lengths $L_a$ and $L_b$. The proximal end of the first pull wire 20a is operably coupled to the first moment arm 100a, while the proximal end of the second pull wire 20b is operably coupled to the second moment arm 100b.

The mechanical energy transmission linkage 18a further comprises a drive assembly 102 operably coupled to the moment arms 100a, 100b. The control mechanism 16 is configured for applying a linear input force F, and in this case a tensile input, to the drive assembly 102 in a manner that creates the same moment M on the moment arms 100a, 100b, such that the first moment arm 100a applies a first tensile output $T_a$ to the proximal end of the first pull wire 20a, and the second moment arm 100b applies a second tensile output $T_b$ to the proximal end of the second pull wire 20b, in accordance with the preset pull wire tension ratio.

It can be appreciated that the first tensile output $T_a$ is a linear function of the length $L_a$ and moment M of the first moment arm 100a, in accordance with the equation:

$$T_a = M/L_a$$

and similarly, the second tensile output $T_b$ is a linear function of the length $L_b$ and moment M of the second moment arm 100b, in accordance with the equation:

$$T_b = M/L_b$$

The ratio between the first tensile output $T_a$ and the second tensile output $T_b$ can be characterized as:

$$T_a/T_b = \frac{M/L_a}{M/L_b} = L_b/L_a$$

Thus, the pull wire tension output ratio of the mechanical energy transmission linkage 18a can be preset by setting the respective lengths of the moment arms 100a, 100b, with the tensile outputs $T_a$, $T_b$ being inversely proportional to the lengths $L_a$, $L_b$ of the moment arms 100a, 100b with which they are respectively associated. In the illustrated embodiment, the respective lengths $L_a$, $L_b$ of the moment arms 100a, 100b are unequal, so that the pull wire tension ratio of the mechanical energy transmission linkage 18a is different than unity.

In the illustrated embodiment, the length $L_a$ of the first moment arm 100a is less than the length $L_b$ of the second moment arm 100b, such that the first tensile output $T_a$ applied to the proximal end of the first pull wire 20a is greater than the second tensile output $T_b$ applied to the proximal end of the second pull wire 20b (i.e., the pull wire tension ratio of the mechanical energy transmission linkage 18a will be greater than unity). As a result, because the pull wires 20a, 20b are respectively associated with the proximal bend 30 and the distal end 32 of the compound curve 28 assumed by the distal end 26 of the catheter body 12, the extent of the proximal bend 30 will be greater than the extent of the distal bend 32.

Of course, in the alternative case where the length $L_a$ of the first moment arm 100a is greater than the length $L_b$ of the second moment arm 100b the first tensile output $T_a$ applied to the proximal end of the first pull wire 20a will be less than the second tensile output $T_b$ applied to the proximal end of the second pull wire 20*b* (i.e., the pull wire tension ratio of the mechanical energy transmission linkage 18*a* will be less than unity). As a result, because the pull wires 20*a*, 20*b* are respectively associated with the proximal bend 30 and the distal end 32 of the compound curve 28 assumed by the distal end 26 of the catheter body 12, the extent of the proximal bend 30 will be less than the extent of the distal bend 32.

It should be appreciated that if more than two pull wires 20*a*, 20*b* are used (i.e., the complex curve 28 has more than two bends), the mechanical transmission linkage 18*a* may be modified to include additional moment arms 100 (i.e., one additional moment arm for each additional pull wire) to which the proximal ends of the additional pull wires 20*a*, 20*b* are operably coupled, and to which the control mechanism 16 applies the same moment M.

Figure 8:
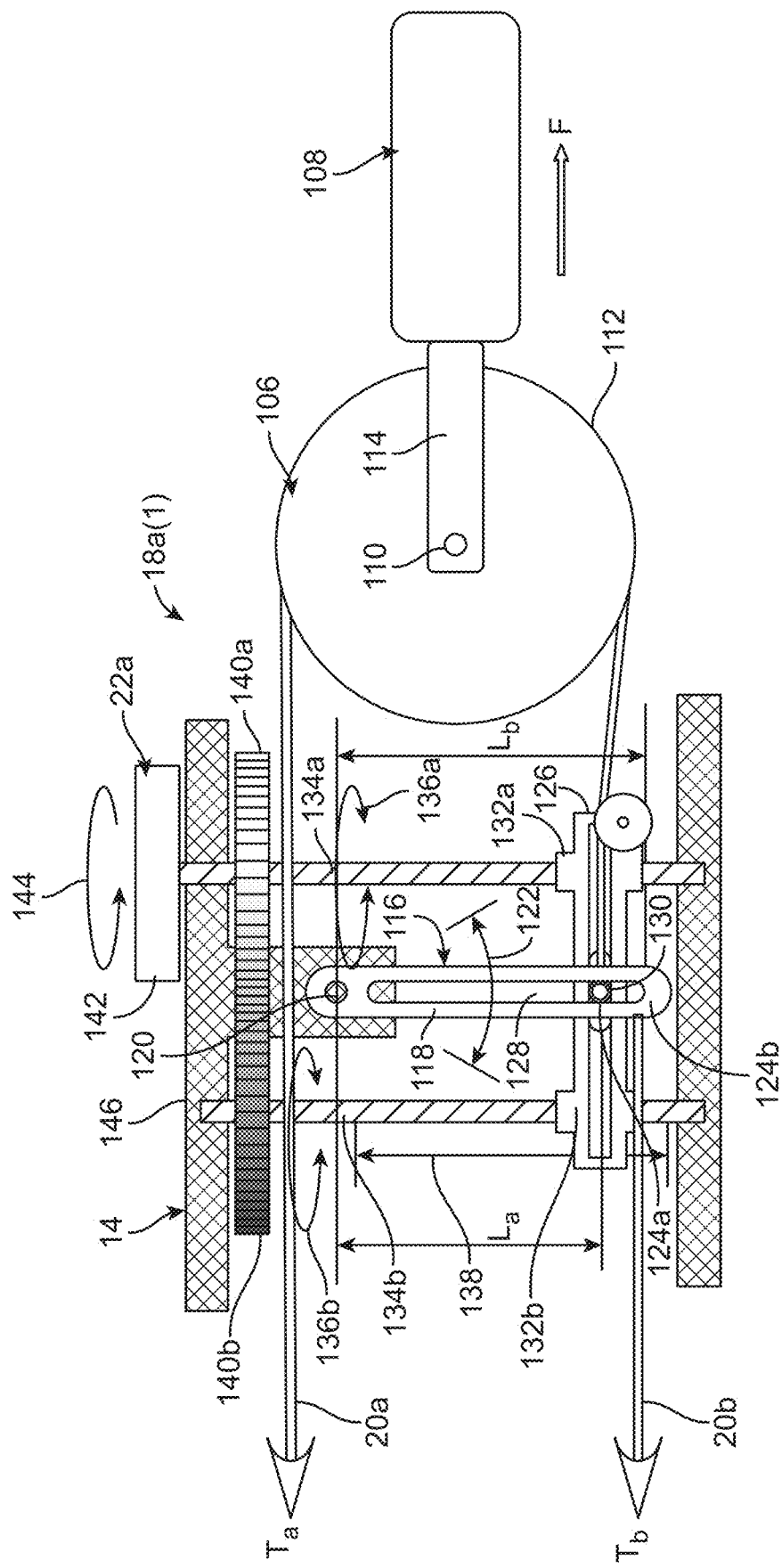
FIG. 8 is a plan view of one specific embodiment of the mechanical transmission linkage of FIG. 7.

Referring now to FIG. 8, one specific embodiment of a mechanical transmission linkage 18*a*(1) that simultaneously applies two tensile outputs $T_a$, $T_b$ respectively to the proximal ends of the two pull wires 20*a*, 20*b* in accordance with a preset pull wire tension ratio will be described.

The mechanical transmission linkage 18*a*(1) comprises a pulley 106 and a yoke 108 that correspond to the drive assembly 102 of the mechanical transmission linkage 18*a* of FIG. 7. The pulley 106 comprises an axle 110 to which the control mechanism 16 applies the linear input force F (in this case, a tensile input), and a wheel 112 around which the proximal end of the first pull wire 20*a* is looped. The yoke 108 comprises two arms 114 (only one illustrated) between which the axle 110 of the pulley 106 is rotatably affixed.

The mechanical transmission linkage 18*a* further comprises a lever 116 having lever arm 118 and a hinge 120 (corresponding to the axis 104 in FIG. 7) about which the lever arm 118 rotates (shown by the arrow 122). The proximal end of the first pull wire 20*a* is engaged to the lever arm 118 at a first anchor point 124*a* to create the first moment arm 100*a* illustrated in FIG. 7 (with the length $L_a$ of the first moment arm 100*a* being equal to the distance between the hinge 120 and the first anchor point 124*a*), and the proximal end of the second pull wire 20*b* is engaged to the lever arm 118 at a second anchor point 124*b* to create the second moment arm 100*b* illustrated in FIG. 7 (with the length $L_b$ of the second moment arm 100*b* being equal to the distance between the hinge 120 and the second anchor point 124*b*).

Thus, when the control mechanism 16 applies the tensile input F to the axle 108 of the pulley 106 via the yoke 110, the first tensile output $T_a$ will be applied to the proximal end of the first pull wire 20*a* by the lever arm 118 at the first anchor point 124*a*, while the second tensile output $T_b$ will be applied to the proximal end of the second pull wire 20*b* by the lever arm 118 at the second anchor point 124*b*, in accordance with the preset pull wire tension ratio. The preset pull wire tension ratio of the mechanical transmission linkage 18*a* illustrated in FIG. 8 (i.e., the ratio between the tensile outputs $T_a$, $T_b$) is defined in equation [3] above. The first anchor point 124*a* is located between the second anchor point 124*b* and the hinge 120, such that the length $L_a$ of the first moment arm 100*a* (shown in FIG. 7) associated with the first pull wire 20*a* is less than the length $L_b$ of the second moment arm 100*b* (shown in FIG. 7) associated with the second pull wire 20*b*. Thus, the preset pull wire ratio of the first tensile output $T_a$ over the second tensile output $T_b$ will always be greater than unity in this embodiment.

In the illustrated embodiment, the preset pull wire tension ratio of the mechanical transmission linkage 18*a* is adjustable. In particular, the proximal end of the first pull wire 20*a* is slidably engaged to the lever arm 118, such that the first anchor point 124*a* is adjustable along a length of the lever arm 118 to adjust the length $L_a$ of the first moment arm 100*a*, and thus, the preset pull wire tension ratio of the first tensile output $T_a$ over the second tensile output $T_b$. To this end, the mechanical transmission linkage 18*a* further comprises a wire tension ratio adjustment mechanism 22*a* configured for adjusting the first anchor point 124*a* along the length of the lever arm 118.

To this end, the wire tension ratio adjustment mechanism 22*a* comprises a slider carriage 126 to which the proximal end of the first pull wire 20*a* is affixed. The slider carriage 126 is configured for being displaced along the lever arm 118 to adjust the first anchor point 124*a* along the length of the lever arm 118. The lever arm 118 has a lengthwise slot 128 and the slider carriage 126 has a protuberance 130 (corresponding to the first anchor point 124*a*) to which the proximal end of the first pull wire 20*a* is affixed. The protuberance 130 of the slider carriage 126 is configured for slidably engaging the slot 128 of the lever arm 118, so that the first anchor point 124*a* may be moved up or down the slot 128 of the lever arm 118. In the illustrated embodiment, the slider carriage 126 comprises a first collar 132*a* and a second collar 132*b* transversely straddling the lever arm 118. The wire tension ratio adjustment mechanism 22*a* further comprises a first rod 134*a* and a second rod 134*b* respectively disposed through the first collar 132*a* and the second collar 132*b*. The collars 132*a*, 132*b* are interiorly threaded, while the rods 134*a*, 134*b* are exteriorly threaded, such that the first collar 132*a* and the first rod 134*a* are threadedly engaged with other, and the second collar 132*b* and the second rod 134*b* are threadedly engaged with other. Thus, rotation of the rods 130*a*, 130*b* along their axes (shown by the arrows 136*a*, 136*b*) will linearly displace the slider carriage 126 up or down (shown by the arrow 138) along the rods 130 depending on the direction of rotation of the rods 130*a*, 130*b*.

The wire tension ratio adjustment mechanism 22*a* further comprises circular drive gear 140*a* affixed to the first rod 134*a*, and a circular idle gear 140*b* affixed to the second rod 134*b*. The circular drive gear 140*a* and the circular idle gear 140*b* are engaged with each other, such that rotation of the first rod 134*a* (shown by the arrow 134*a*) causes the second rod 134*b* to rotate in the opposite direction (shown by the arrow 134*b*) via the engagement between the circular drive gear 140*a* and the circular idle gear 140*b*, thereby linearly displacing the slider carriage 126 along the lever arm 118 (shown by the arrow 136). Because the rotation of the drive gear 140*a*, and thus the first rod 134*a*, in one direction causes the rotation of the idle gear 140*b*, and thus the second rod 134*b*, in an opposite direction, the threads on the first rod 134*a* is counter wound to the threads on the second rod 134*b*, such that rotation of the rods 134 work in unison to linearly displace the slider carriage 126 along the lever arm 118. The hinge 120 of the lever 116 is affixed relative to a frame 146, and the threaded rods 134 are rotatably affixed to the frame 146. The wire tension ratio adjustment mechanism 22*a* further comprises a control dial 142 affixed to the first rod 134*a*, such that rotation of the control dial 138 in a direction (shown by the arrow 144) rotates the first rod 134*a* (shown by the arrow 136*a*), and thus the second rod 134*b* (shown by the arrow 136*b*) via the engagement between the circular drive gear 140*a* and circular idle gear 140*b*, ultimately linearly displacing the slider carriage 126 along the lever arm 118. The control dial 142 may be disposed on the exterior of the handle 14 (shown in FIGS. 6A and 6B).

Figure 9:
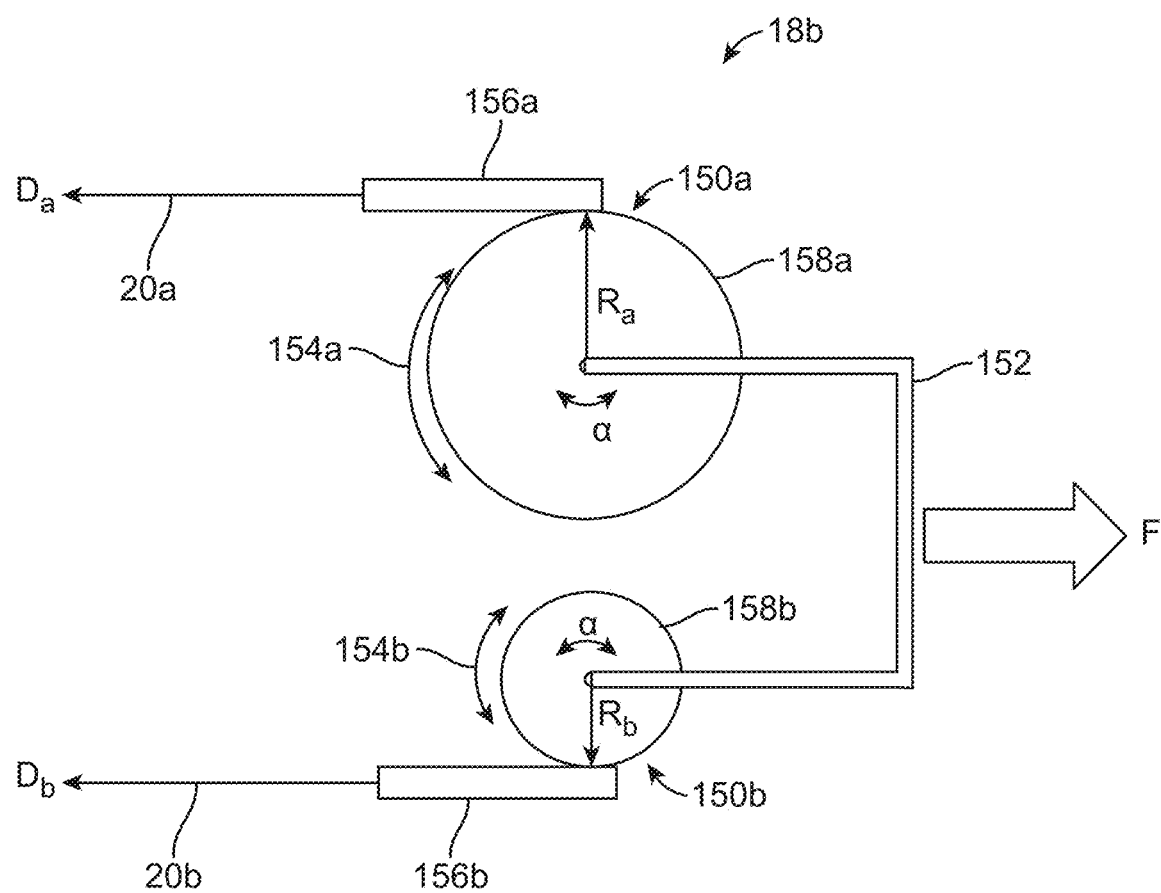
FIG. 9 is a plan view of another embodiment of a mechanical transmission linkage used in the catheter of FIG. 1A.

Referring now to FIG. 9, another exemplary embodiment of a mechanical energy transmission linkage 18b will be described. The mechanical transmission linkage 18b is configured, in response to an input force F by the control mechanism 16 (shown in FIG. 1), for simultaneously applying two linear displacement outputs $D_a$, $D_b$ respectively to the proximal ends of the two pull wires 20a, 20b in accordance with a preset pull wire displacement ratio. This should be contrasted with the mechanical energy transmission linkage 18a illustrated in FIG. 7, which simultaneously applies two tensile outputs $T_a$, $T_b$ respectively to the proximal ends of the two pull wires 20a, 20b in accordance with a preset pull wire tension ratio.

The mechanical energy transmission linkage 18b utilizes a plurality of cams 150 to create a preset pull wire linear displacement ratio between the pull wires 20, and in particular, two cams 150a, 150b that transform rotational motion (shown by arrows 154a, 154b) into linear motion to create a preset pull wire linear displacement ratio between the two pull wires 20a, 20b. The proximal end of the first pull wire 20a is operably coupled to the first cam 150a, while the proximal end of the second pull wire 20b is operably coupled to the second cam 150b. The mechanical energy transmission linkage 18b further comprises a drive assembly 152 operably coupled to the cams 150a, 150b. The control mechanism 16 is configured for applying an input force F to the drive assembly 152, such that the first cam 150a applies a linear displacement output $D_a$ to the proximal end of the first pull wire 20a, and the second cam 150b applies a linear displacement output $D_b$ to the proximal end of the second pull wire 20b, in accordance with the preset pull wire displacement ratio. That is, the cams 150a, 150b transform rotational energy provided to the cams 150a, 150b by the drive assembly 152 into linear motion to apply linear displacement outputs of $D_a$, $D_b$ to the proximal ends of the respective first and second pull wires 20a, 20b.

In the illustrated embodiment, the first cam 150a comprises a first linear element 156a to which the proximal end of the first pull wire 20a is affixed, and a first rotary element 158a engaged with the drive assembly 152. The second cam 150b comprises a second linear element 156b to which the proximal end of the second pull wire 20b is affixed, and a second rotary element 158b engaged with the drive assembly 152. The rotary elements 158a, 158b respectively have radii $R_a$ and $R_b$. The drive assembly 152 rotates the first cam 150a and the second cam 150b at the same angular displacement α. In this case, it can be appreciated that the first linear displacement $D_a$ is a linear function of the radius $R_a$ of the first cam 150a, in accordance with the equation:

$$D_a = \frac{2\pi R_a \alpha}{360}$$

and similarly, the second linear displacement $D_b$ is a linear function of the radius $R_b$ of the second cam 150b, in accordance with the equation:

$$D_b = \frac{2\pi R_b \alpha}{360}$$

The ratio between the first linear displacement $D_a$ and the second linear displacement $D_b$ can be characterized as:

$$D_a/D_b = \frac{\frac{2\pi R_a \alpha}{360}}{\frac{2\pi R_b \alpha}{360}} = R_a/R_b$$

Thus, the displacement ratio of the mechanical energy transmission linkage 18b can be preset by setting the respective radii $R_a$, $R_b$ of the rotary elements 158a, 158b, with the linear displacement outputs $D_a$, $D_b$ being directly proportional to the radii $R_a$, $R_b$ of the rotary elements 158a, 158b of the cams 150a, 150b with which they are respectively associated. In the illustrated embodiment, the respective radii $R_a$, $R_b$ of the rotary elements 158a, 158b are unequal, so that the pull wire displacement ratio of the mechanical energy transmission linkage 18b is different than unity.

In the illustrated embodiment, the radius $R_a$ of the first rotary element 158a is greater than the radius $R_b$ of the second rotary element 158b, such that the first linear displacement output $D_a$ applied to the proximal end of the first pull wire 20a is greater than the second linear displacement output $D_b$ applied to the proximal end of the second pull wire 20b (i.e., the pull wire displacement ratio of the mechanical energy transmission linkage 18b will be greater than unity). As a result, because the pull wires 20a, 20b are respectively associated with the proximal bend 30 and the distal end 32 of the compound curve 28 assumed by the distal end 26 of the catheter body 12, the extent of the proximal bend 30 will be greater than the extent of the distal bend 32.

Of course, in the alternative case where the radius $R_a$ of the first rotary element 158a is less than the radius $R_b$ of the second rotary element 158b, the first linear displacement output $D_a$ applied to the proximal end of the first pull wire 20a will be less than the second linear displacement output $D_b$ applied to the proximal end of the second pull wire 20b (i.e., the pull wire displacement ratio of the mechanical energy transmission linkage 18b will be less than unity). As a result, because the pull wires 20a, 20b are respectively associated with the proximal bend 30 and the distal end 32 of the compound curve 28 assumed by the distal end 26 of the catheter body 12, the extent of the proximal bend 30 will be less than the extent of the distal bend 32.

It should be appreciated that if more than two pull wires 20a, 20b are used (i.e., the complex curve 28 has more than two bends), the mechanical transmission linkage 18b may be modified to include additional cams 150 (i.e., one additional cam for each additional pull wire) to which the proximal ends of the additional pull wires 20a, 20b are operably coupled, and to which the control mechanism 16 applies the input force F via the drive assembly 152.

Figure 10:
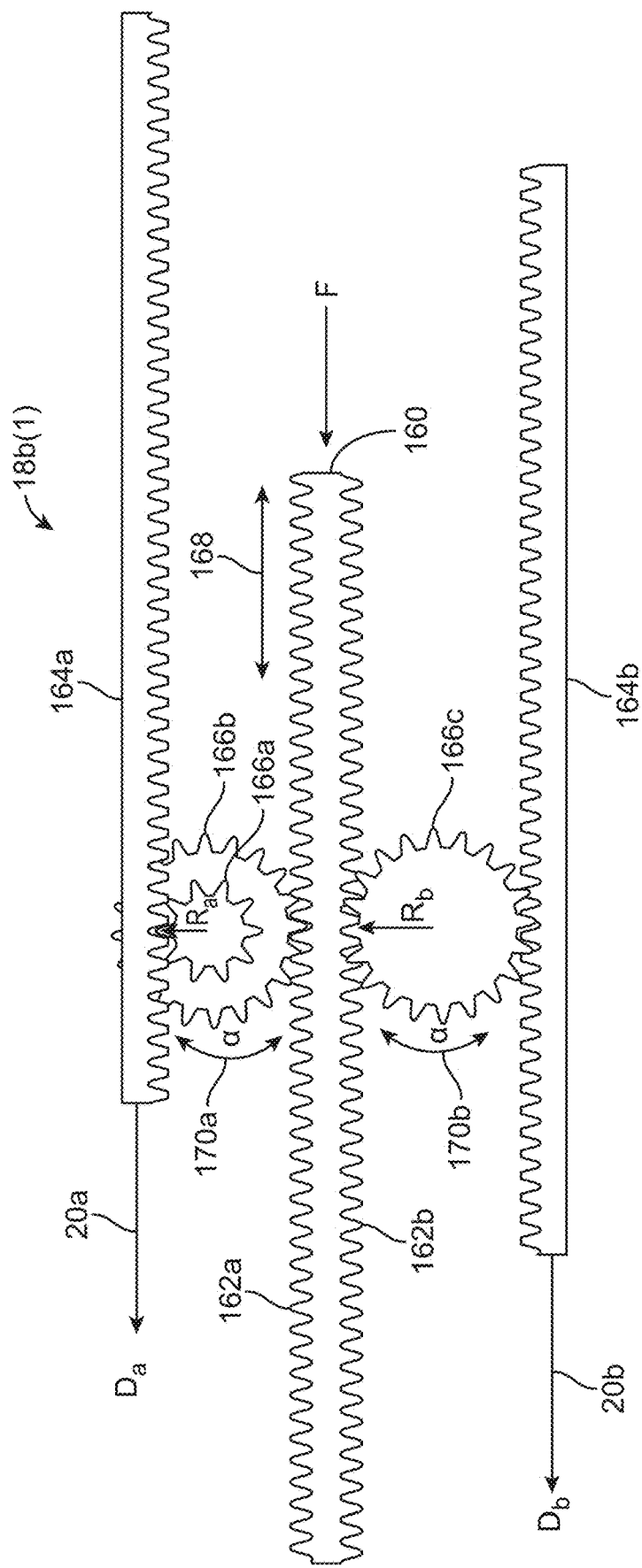
FIG. 10 is a plan view of one specific embodiment of the mechanical transmission linkage of FIG. 9.
Figure 11:
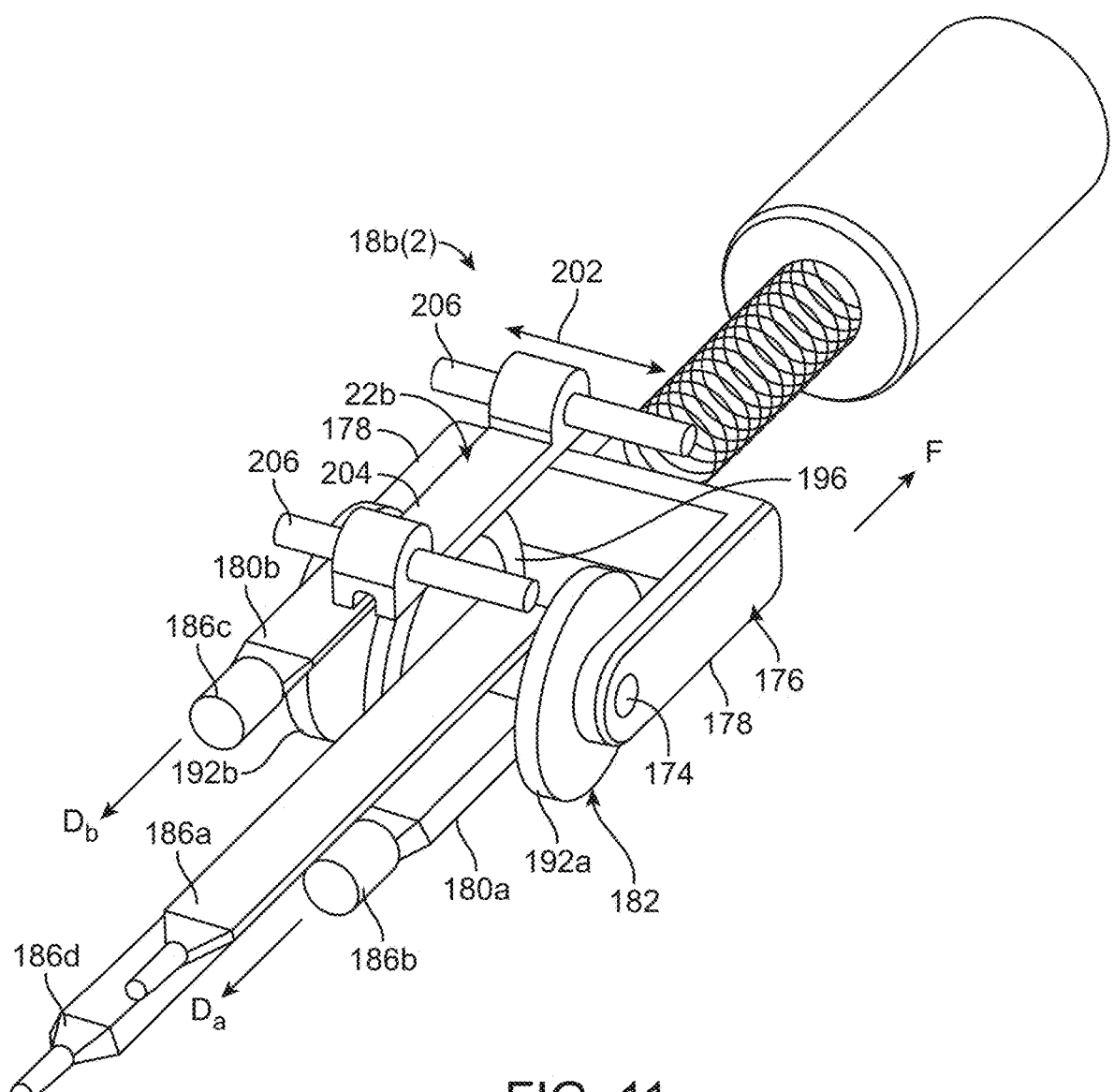
FIG. 11 is a perspective view of another specific embodiment of the mechanical transmission linkage of FIG. 9.
Figure 12:
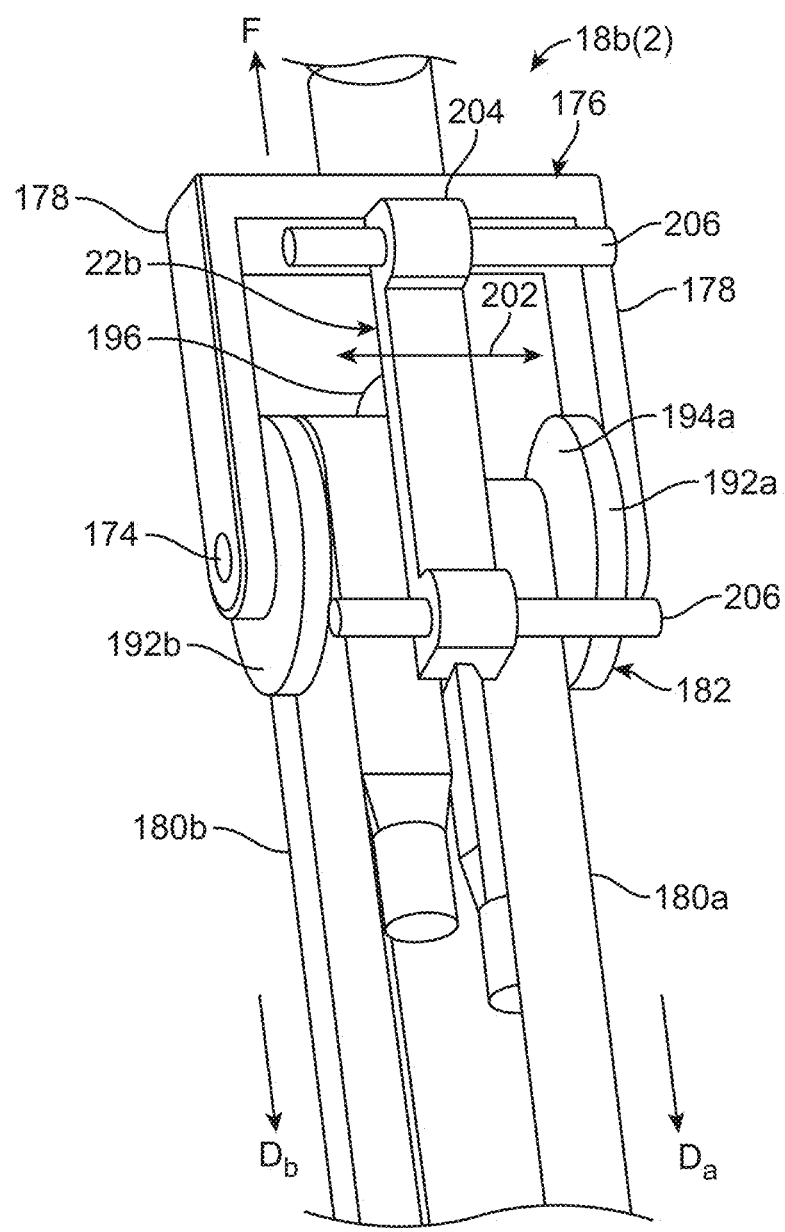
FIG. 12 is a partially cutaway perspective view of the mechanical transmission linkage of FIG. 11.

Referring now to FIG. 10, one specific embodiment of a mechanical transmission linkage 18b(1) that simultaneously applies two linear displacement outputs $D_a$, $D_b$ respectively to the proximal ends of the two pull wires 20a, 20b in accordance with a preset pull wire displacement ratio will be described.

The mechanical transmission linkage 18b(1) comprises a linear drive rack 160 that corresponds to the drive assembly 152 of the mechanical transmission linkage 18b of FIG. 9. The control mechanism 16 (shown in FIG. 1) may be coupled to an intervening element for applying the input force F (and in this case, a linear input force) to the linear drive rack 160. The linear drive rack 160 has a first geared side 162a and a second geared side 162b opposite the first geared side 162a. The mechanical transmission linkage 18b(1) further comprises a first linear gear 164a and a second linear gear 164b that respectively correspond to the first linear element 156a and the second linear element 156b of the mechanical transmission linkage 18b of FIG. 9, a first rotary gear 166a and a second rotary gear 166b that correspond to the first rotary element 158a of the mechanical transmission linkage 18b of FIG. 9, and a third rotary gear 166c that corresponds to the second rotary element 158b of the mechanical transmission linkage 18b of FIG. 9. The first linear gear 164a is affixed to the proximal end of the first pull wire 20a, and the second linear gear 164b is affixed to the proximal end of the second pull wire 20b. The second rotary gear 166b is fixed in relation to the first rotary gear 166a. The first rotary gear 166a is engaged with the first linear gear 164a. The second rotary gear 166b is engaged with the first geared side 162a of the linear drive rack 160. The third rotary gear 166c is engaged between the second linear gear 164b and the second geared side 162b of the linear drive rack 160.

When the control mechanism 16 applies the input force F to the linear drive rack 160, the linear drive rack 160 is linearly displaced (shown by the arrow 168), such that the first rotary gear 166a and the second rotary gear 166b rotate in unison to linearly displace the first linear gear 164a, thereby applying the first linear displacement output $D_a$ to the proximal end of the first pull wire 20a, and the third rotary gear 166c rotates in an opposite direction to 166a, 166b (shown by the arrows 170a, 170b) to linearly displace the second linear gear 164b, thereby applying the second linear displacement output $D_b$ to the proximal end of the second pull wire 20b, in accordance with the preset pull wire displacement ratio.

The preset pull wire displacement ratio of the mechanical transmission linkage 18b(1) illustrated in FIG. 10 (i.e., the ratio between the first linear displacement output $D_a$ and the second linear displacement output $D_b$) is defined in equation [6] above. The ratio between the first linear displacement output $D_a$ and the second linear displacement output $D_b$ can also be defined as the number of teeth of the first rotary gear 166a divided by the number of teeth of the third rotary gear 166c. The first rotary gear 166a has a radius $R_a$, and each of the second rotary gear 166b and the third rotary gear 166c has a radius $R_b$. Because the second rotary gear 166b and the third rotary gear 166c have the same radius $R_b$ (i.e., the number of teeth in the second rotary gear 166b is the same as the number of teeth in the third rotary gear 166c), the angular displacements α that the second rotary gear 166b (and thus, the first rotary gear 166a) and the third rotary gear 166c are displaced by linear displacement of the linear drive rack 160 will always be the same. However, the first rotary gear 166a has a radius $R_a$ that is different from the radius $R_b$ of the third gear 164c (i.e., the number of teeth in the first rotary gear 166a is different from the radius $R_b$ of the third gear 164c). Thus, the preset pull wire linear displacement ratio of the first linear displacement $D_a$ over the second linear displacement $D_b$ will be different than unity. In this embodiment, the radius $R_a$ of the first rotary gear 166a is less than the radius $R_b$ of the third gear 164c, in which case, the preset pull wire linear displacement ratio of the first linear displacement $D_a$ over the second linear displacement $D_b$ will be less than unity. In alternative embodiments, the radius $R_a$ of the first rotary gear 166a may be greater than the radius $R_b$ of the third gear 164c, in which case, the preset pull wire linear displacement ratio of the first linear displacement $D_a$ over the second linear displacement $D_b$ will be greater than unity.

Referring now to FIGS. 11-16, another specific embodiment of a mechanical transmission linkage 18b(2) that simultaneously applies two linear displacement outputs $D_a$, $D_b$ respectively to the proximal ends of the two pull wires 20a, 20b in accordance with a preset pull wire displacement ratio will be described.

The mechanical transmission linkage 18b(2) comprises an axle 174 and a yoke 176 that corresponds to the drive assembly 152 of the mechanical transmission linkage 18b of FIG. 9. As best shown in FIGS. 11-14, the yoke 176 comprises two arms 178 between which the axle 174 is rotatably affixed. The control mechanism 16 (shown in FIG. 1) is coupled to the yoke 176 for applying the input force F, and in particular a tensile input, to the axle 174.

The mechanical transmission linkage 18b(2) further comprises a first belt 180a and a second belt 180b that respectively correspond to the first linear element 156a and the second linear element 156b of the mechanical transmission linkage 18b of FIG. 9. As best shown in FIGS. 15 and 16, the mechanical transmission linkage 18b(2) further comprises a wheel assembly 182 having a first annular groove 184a and a second annular groove 184 that respectively correspond to the first rotary element 158a and the second rotary element 158b of the mechanical transmission linkage 18b of FIG. 9. The first belt 180a is looped around the first annular groove 184a of the wheel assembly 182 to form a first distal end 186a coupled to the proximal end of the first pull wire 20a and a second distal end 186b coupled to a first anchor point 188a, and the second belt 180b is looped around the second annular groove 184b of the wheel assembly 182 to form a first distal end 186c coupled to the proximal end of the second pull wire 20b and a second distal end 186d coupled to a second anchor point 188b. The first belt 180a and second belt 180b are looped around the respective first and second annular grooves 184a, 184b in the same rotational direction.

Thus, when the control mechanism 16 applies the tensile input F to the axle 174, the wheel assembly 182 rotates with the axle 174 (shown by the arrow 190), and thus, the first annular groove 184a rotates to linearly displace the first belt 180a, thereby applying the first linear displacement output $D_a$ to the proximal end of the first pull wire 20a, and the second annular groove 184b rotates to linearly displace the second belt 180b, thereby applying the second linear displacement output $D_b$ to the proximal end of the second pull wire 20b, in accordance with the preset pull wire tension ratio.

The preset pull wire displacement ratio of the mechanical transmission linkage 18b(2) illustrated in FIGS. 11-16 (i.e., the ratio between the first linear displacement output $D_a$ and the second linear displacement output $D_b$) is defined in equation [6] above. As best shown in FIG. 16, the first looped belt 180a has a first radius $R_a$ (i.e., the first annular groove 184a has an effective radius $R_a$), and the second looped belt 180b has a second radius $R_b$ (i.e., the second annular groove 184b has an effective radius $R_b$). Because the first annular groove 184a and the second annular groove 184b rotate together about the same axle 174, the angular displacements α that the looped belts 180a, 180b are displaced by rotation of the axle 174 will always be the same. However, the radius $R_a$ of the first annular groove 184a is different from the radius $R_b$ of the second annular groove 184b. Thus, the preset pull wire linear displacement ratio of the first linear displacement $D_a$ over the second linear displacement $D_b$ will be different than unity. In this embodiment, the radius $R_a$ of the first annular groove 184a is less than the radius $R_b$ of the second annular groove 184b, in which case, the preset pull wire linear displacement ratio of the first linear displacement $D_a$ over the second linear displacement $D_b$ will be less than unity. In alternative embodiments, the radius $R_a$ of the first annular groove 184a may be greater than the radius $R_b$ of the second annular groove 184b, in which case, the preset pull wire linear displacement ratio of the first linear displacement $D_a$ over the second linear displacement $D_b$ will be greater than unity.

In the illustrated embodiment, the preset pull wire tension ratio of the mechanical transmission linkage 18b(2) is adjustable. In particular, the effective radii $R_a$, $R_b$ of the annular grooves 184a, 184b are adjustable. As best shown in FIGS. 11-14, the mechanical transmission linkage 18b(2) further comprises a pull wire displacement ratio adjustment mechanism 22b configured for adjusting the effective radii $R_a$, $R_b$ of both the annular grooves 182a, 182b in an inversely proportional manner.

Figure 13:
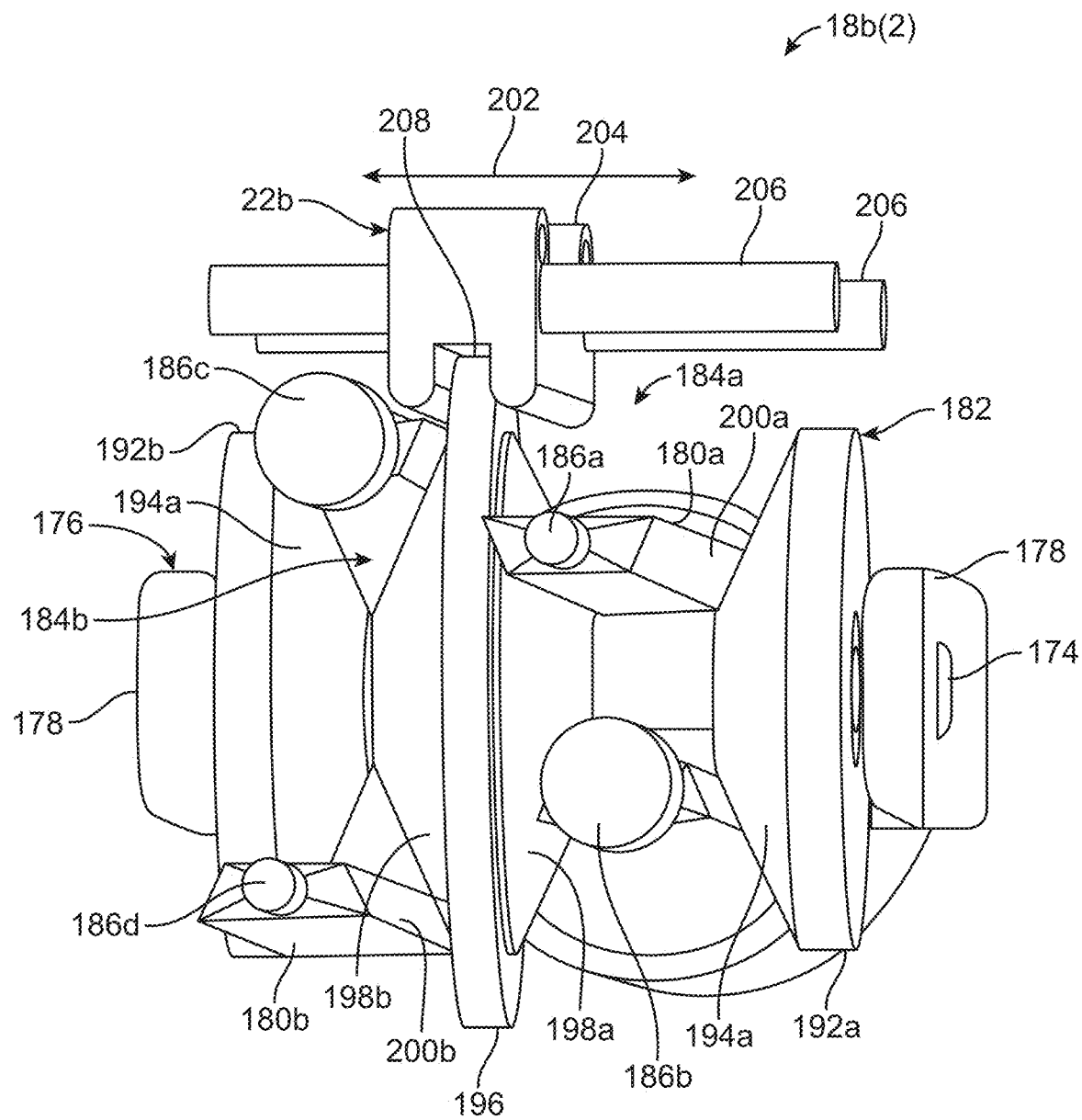
FIG. 13 is a front view of the mechanical transmission linkage of FIG. 11.
Figure 14:
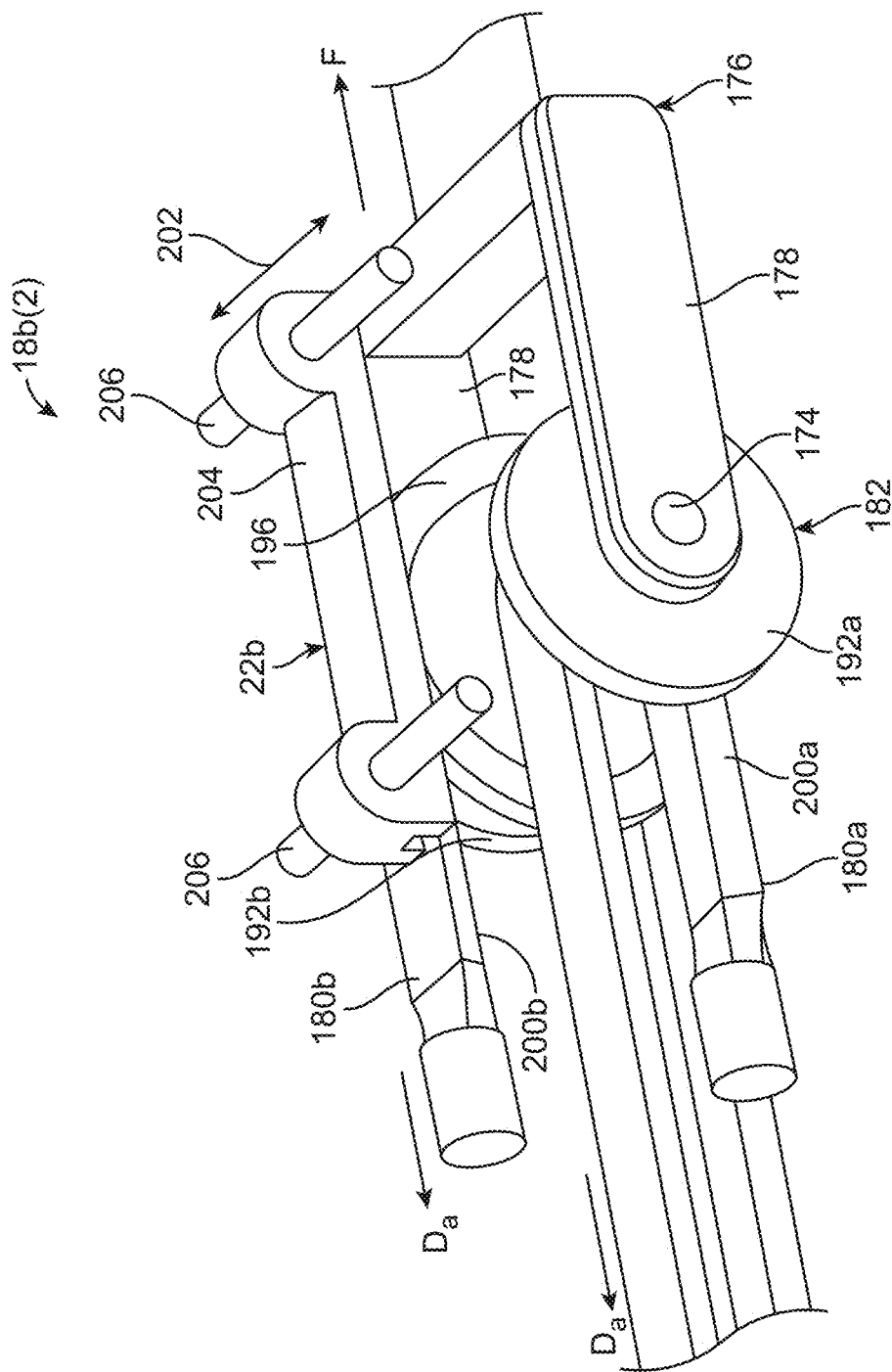
FIG. 14 is another partially cutaway perspective view of the mechanical transmission linkage of FIG. 11.

To this end, the wheel assembly 182 comprises a first outer plate 192a and a second outer plate 192b disposed on the axle 174. As best shown in FIGS. 13 and 15, the outer plates 192a, 192b respectively have convex conical surfaces 194a, 194b that face each other. The wheel assembly 182 further comprises an inner plate 196 disposed on the axle 174 between the outer plates 192a, 192b. As best shown in FIGS. 13 and 15, the inner plate 196 has opposing first and second convex conical surfaces 198a, 198b that respectively face the outer places 194a, 194b. In the illustrated embodiment, the outer plates 192a, 192b, as well as the inner plate 196, are rotatably affixed to the axle 174 (i.e., the outer plates 192a, 192b and inner plate 196 rotate with the axle 174). The outer plates 192a, 192b are laterally affixed to the axle 174 (i.e., the outer plates 192a, 192b cannot laterally slide along the axle 174), while the inner plate 198 is slidably disposed laterally along the axle 174 (i.e., the inner plate 198 can laterally slide along the axle 174). The inner plate 196 may, e.g., have a protruding pin (not shown) that slides along a groove (not shown) of the axle 174 to allow the inner plate 198 to laterally slide along the axle 174, while preventing the inner plate 198 from rotating relative to the axle 174.

As best shown in FIG. 15, the first belt 180a has inwardly angled opposing surfaces 200a that respectively conform to the convex conical surface 194a of the first outer plate 192a and the first convex conical surface 198a of the inner plate 196, thereby setting a first radius of the first looped belt 180a; and the second belt 180b has inwardly angled opposing surfaces 200b that respectively conform to the convex conical surface 198b of the second outer plate 192b and the second convex conical surface 198b of the inner plate 196, thereby setting a second radius of the second looped belt 180b. In the illustrated embodiment, each of the belts 178 has a trapezoidal cross-section that forms the respective angled opposing surfaces 200.

The pull wire displacement ratio adjustment mechanism 22b is configured for laterally sliding the inner plate 196 along the axle 174 (shown by the arrow 202 in FIG. 15). In the illustrated embodiment shown in FIGS. 11-14, the pull wire displacement ratio adjustment mechanism 22b comprises a slider carriage 204 configured for being displaced along a direction of the axle 174. The pull wire displacement ratio adjustment mechanism 22b further comprises a pair of rails 206 extending in the direction along the axle 174. The slider carriage 204 is configured for sliding along the pair of rails 206. As best shown in FIG. 13, the slider carriage 204 has a groove 208 in which an outer radial portion of the inner plate 196 is disposed, such that displacement of the slider carriage 204 correspondingly slides the inner plate 196 along the axle 174. The pull wire displacement ratio adjustment mechanism 22b may further comprise a control slider (not shown) affixed to the slider carriage 204, such that sliding the control slider slides the slider carriage 204. Such control slider may be disposed on the exterior of the handle 14.

As a result, the width of the first annular groove 184a is modified, thereby modifying the radius $R_a$ of the first looped belt 180a, such that the first pull wire displacement $D_a$ changes, while the width of the second annular groove 184b is modified in inverse proportion to the modified width of the first annular groove 184b, thereby modifying the radius $R_b$ of the second looped belt 180b in inverse proportion to the modified radius $R_a$ of the first looped belt 180a, such that the second pull wire displacement $D_b$ is modified in inverse proportion to the first pull wire displacement $D_a$.

For example, as best shown in FIG. 15, when the inner plate 196 is slid along the axle 174 (rightward along the arrow 202), the width of the first annular groove 184a decreases, while the width of the second annular groove 184b increases. As a result, the first looped belt 180a is squeezed between the convex conical surface 194a of the first outer plate 192a and the first convex conical surface 198a of the inner plate 196. This action displaces the first looped belt 180a radially outward (upward along the arrow 210a) in opposition to the spring-loaded tensile forces on the first looped belt 180a, thereby increasing its radius $R_a$ and correspondingly increasing the first pull wire displacement $D_a$. At the same time, the second looped belt 180b is released between the convex conical surface 198a of the second outer plate 192b and the second convex conical surface 198b of the inner plate 196. This action displaces the second looped belt 180b radially inward (downward along the arrow 210b) facilitated by the spring-loaded tensile forces on the second looped belt 180b, thereby decreasing its radius $R_b$ and correspondingly decreasing the second pull wire displacement $D_b$. In this case, the preset pull wire displacement ratio increases.

In contrast, when the inner plate 196 is slid along the axle 174 (leftward along the arrow 202), the width of the first annular groove 184a increases, while the width of the second annular groove 184b decreases. As a result, the first looped belt 180a is released between the convex conical surface 194a of the first outer plate 192a and the first convex conical surface 198a of the inner plate 196. This action displaces the first looped belt 180a radially inward (downward along arrow 210a) facilitated by the spring-loaded tensile forces on the first looped belt 180a, thereby decreasing its radius $R_b$ and correspondingly decreasing the first pull wire displacement $D_a$. At the same time, the second looped belt 180b is squeezed between the convex conical surface 198a of the second outer plate 192b and the second convex conical surface 198b of the inner plate 196. This action displaces the second looped belt 180b radially outward (upward along the arrow 210b) in opposition to the spring-loaded tensile forces on the second looped belt 180b, thereby increasing its radius $R_b$ and correspondingly increasing the second pull wire displacement $D_b$. In this case, the preset pull wire displacement ratio decreases.

Figure 17:
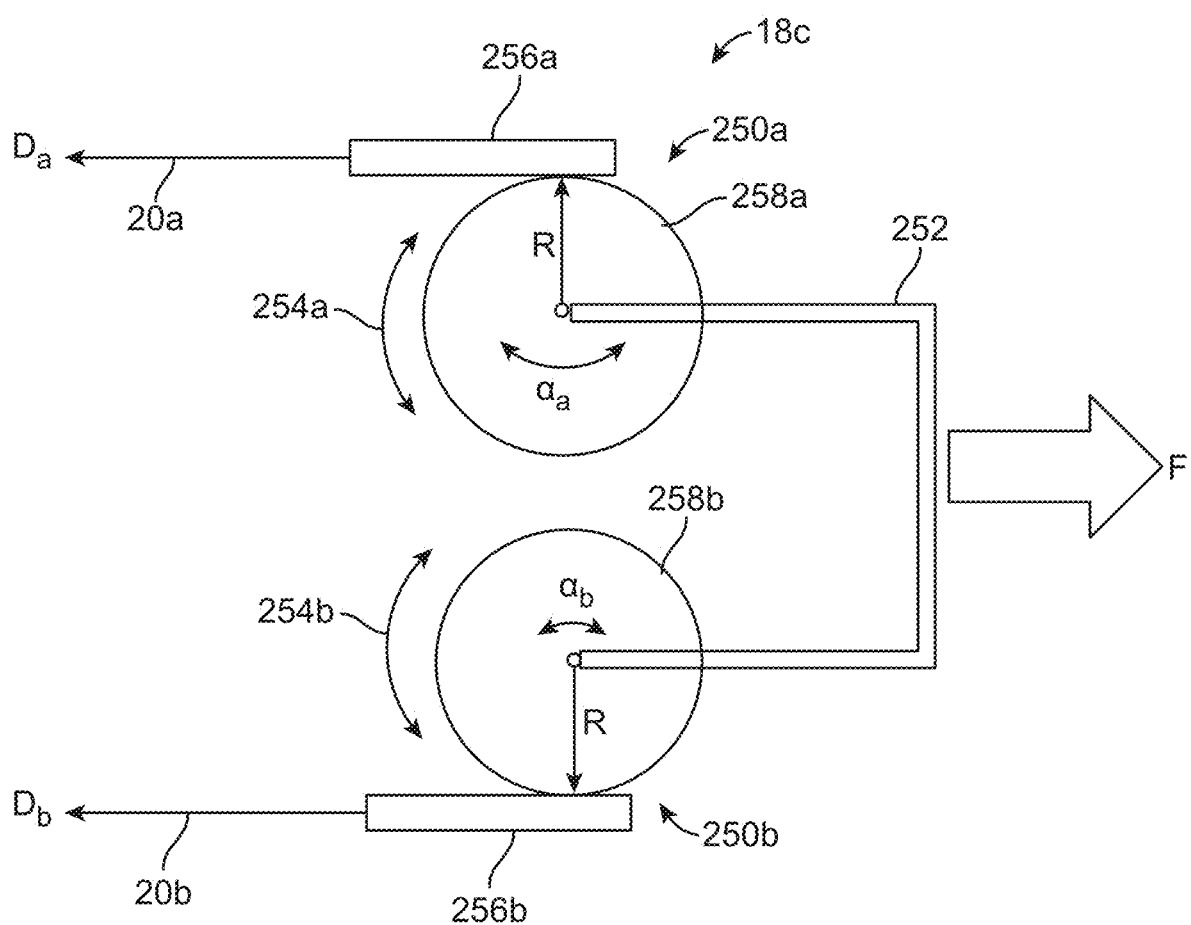
FIG. 17 is a plan view of still another embodiment of a mechanical transmission linkage used in the catheter of FIG. 1A.
Figure 18:
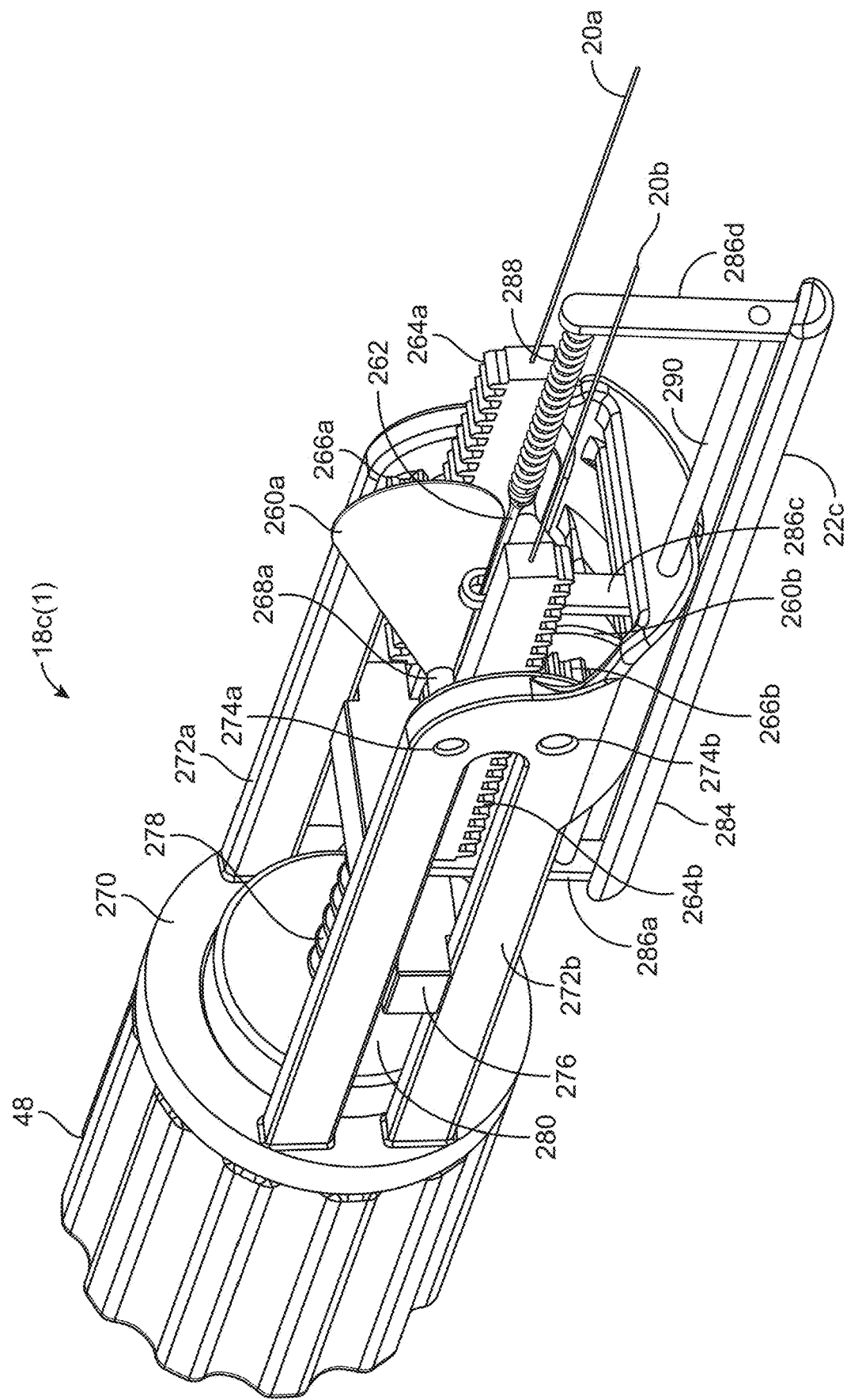
FIG. 18 is a perspective view of a specific embodiment of the mechanical transmission linkage of FIG. 17.

Referring now to FIG. 17, still another exemplary embodiment of a mechanical energy transmission linkage 18c will be described. The mechanical transmission linkage 18c is configured, in response to an input force F by the control mechanism 16 (shown in FIG. 1), for simultaneously applying two linear displacement outputs $D_a$, $D_b$ respectively to the proximal ends of the two pull wires 20a, 20b in accordance with a preset pull wire tension ratio. The mechanical transmission linkage 18c is similar to the mechanical transmission linkage 18b illustrated in FIG. 9. However, unlike the mechanical transmission linkage 18b, which sets the pull wire displacement ratio based on the respective radii of the cams, the mechanical transmission linkage 18c sets the pull wire displacement ratio based on respective angular displacement of the cams.

The mechanical energy transmission linkage 18c utilizes a plurality of cams 250 to create a preset pull wire linear displacement ratio between the pull wires 20, and in particular, two cams 250a, 250b that transform rotational motion (shown by arrows 254a, 254b) into linear motion to create a preset pull wire linear displacement ratio between the two pull wires 20a, 20b. The proximal end of the first pull wire 20a is operably coupled to the first cam 250a, while the proximal end of the second pull wire 20b is operably coupled to the second cam 250b. The mechanical energy transmission linkage 18c further comprises a drive assembly 252 operably coupled to the cams 250. The control mechanism 16 is configured for applying an input force F to the drive assembly 252, such that the first cam 250a applies a linear displacement output $D_a$ to the proximal end of the first pull wire 20a, and the second cam 250b applies a linear displacement output $D_b$ to the proximal end of the second pull wire 20b, in accordance with the preset pull wire displacement ratio. That is, the cams 250 transform rotational energy provided to the cams 250 by the drive assembly 252 into linear motion to apply linear displacement outputs of $D_a$, $D_b$ to the proximal ends of the respective first and second pull wires 20a, 20b.

In the illustrated embodiment, the first cam 250a comprises a first linear element 256a to which the proximal end of the first pull wire 20a is affixed, and a first rotary element 258a engaged with the drive assembly 252. The second cam 250b comprises a second linear element 256b to which the proximal end of the second pull wire 20b is affixed, and a second rotary element 258b engaged with the drive assembly 252. The rotary elements 258a, 258b respectively have the same radii R. The drive assembly 252 rotates cams 250a, 250b at different angular displacements $\alpha_a$, $\alpha_b$.

In this case, it can be appreciated that the first linear displacement $D_a$ is a linear function of the angular displacement $\alpha_a$ of the first cam 250a, in accordance with the equation:

$$D_a = \frac{2\pi R \alpha_a}{360}$$

and similarly, the second linear displacement $D_b$ is a linear function of the angular displacement $\alpha_b$ of the second cam 150b, in accordance with the equation:

$$D_b = \frac{2\pi R \alpha_b}{360}$$

The ratio between the first linear displacement $D_a$ and the second linear displacement $D_b$ can be characterized as:

$$D_a/D_b = \frac{\frac{2\pi R \alpha_a}{360}}{\frac{2\pi R \alpha_b}{360}} = \alpha_a/\alpha_b$$

Thus, the displacement ratio of the mechanical energy transmission linkage 18b can be preset by setting the respective angular displacements $\alpha_a$, $\alpha_b$ of the rotary elements 258a, 258b, with the linear displacement outputs $D_a$, $D_b$ being directly proportional to the angular displacements $\alpha_a$, $\alpha_b$ of the rotary elements 258a, 258b of the cams 250a, 250b with which they are respectively associated. In the illustrated embodiment, the respective angular displacements $\alpha_a$, $\alpha_b$ of the rotary elements 258a, 258b are unequal, so that the pull wire displacement ratio of the mechanical energy transmission linkage 18b is different than unity.

In the illustrated embodiment, the angular displacement $\alpha_a$ of the first rotary element 158a is greater than the angular displacement $\alpha_b$ of the second rotary element 158b, such that the first linear displacement output $D_a$ applied to the proximal end of the first pull wire 20a is greater than the second linear displacement output $D_b$ applied to the proximal end of the second pull wire 20b (i.e., the pull wire displacement ratio of the mechanical energy transmission linkage 18b will be greater than unity). As a result, because the pull wires 20a, 20b are respectively associated with the proximal bend 30 and the distal end 32 of the compound curve 28 assumed by the distal end 26 of the catheter body 12, the extent of the proximal bend 30 will be greater than the extent of the distal bend 32.

Of course, in the alternative case where the angular displacement $\alpha_a$ of the first rotary element 158a is less than the angular displacement $\alpha_b$ of the second rotary element 158b, the first linear displacement output $D_a$ applied to the proximal end of the first pull wire 20a will be less than the second linear displacement output $D_b$ applied to the proximal end of the second pull wire 20b (i.e., the pull wire displacement ratio of the mechanical energy transmission linkage 18b will be less than unity). As a result, because the pull wires 20a, 20b are respectively associated with the proximal bend 30 and the distal end 32 of the compound curve 28 assumed by the distal end 26 of the catheter body 12, the extent of the proximal bend 30 will be less than the extent of the distal bend 32.

It should be appreciated that if more than two pull wires 20a, 20b are used (i.e., the complex curve 28 has more than two bends), the mechanical transmission linkage 18c may be modified to include additional cams 250 (i.e., one additional cam for each additional pull wire) to which the proximal ends of the additional pull wires 20a, 20b are operably coupled, and to which the control mechanism 16 applies the input force F via the drive assembly 252.

Referring now to FIGS. 18-24, one specific embodiment of a mechanical transmission linkage 18c(1) that simultaneously applies two linear displacement outputs $D_a$, $D_b$ respectively to the proximal ends of the two pull wires 20a, 20b in accordance with a preset pull wire displacement ratio will be described.

The mechanical transmission linkage 18c(1) comprises a first cone 260a, a second cone 260b inversely oriented with respect to, and rotatably engaged with, the first cone 260a, and a belt 262 frictionally disposed (i.e., sandwiched) between the cones 260a, 260b. The cones 260a, 260b and the belt 262 correspond to the drive assembly 252 of the mechanical transmission linkage 18c of FIG. 17. The mechanical transmission linkage 18c(1) further comprises a first linear gear 264a (i.e., a rack) and a second linear gear 264b (i.e., a rack) that respectively correspond to the first linear element 256a and the second linear element 256b of the mechanical transmission linkage 18c of FIG. 17, a first rotary gear 266a (i.e., a pinion) that corresponds to the first rotary element 258a of the mechanical transmission linkage 18c of FIG. 17, and a second rotary gear 266b (i.e., a pinion) that corresponds to the second rotary element 258b of the mechanical transmission linkage 18c of FIG. 17. The first rotary gear 266a is affixed relative to the first cone 260a, and the second rotary gear 266b is affixed relative to the second cone 260b, such that the first rotary gear 266a and the first cone 260a rotate in unison, and the second rotary gear 266b and the second cone 260b rotate in unison. The first linear gear 264a is operatively engaged with the first rotary gear 266a, and is affixed to the proximal end of the first pull wire 20a. The second linear gear 264b is operatively engaged with the second rotary gear 266b, and is affixed to the proximal end of the first pull wire 20b.

In the illustrated embodiment, the mechanical transmission linkage 18c(1) comprises a first axle 268a to which the first cone 260a and first rotary gear 266a are affixed, and a second axle 268b to which the second cone 260b and second rotary gear 266b are affixed. Although the first rotary gear 266a is affixed to the first axle 268a adjacent the base (i.e., the circular plane surface) of the first cone 260a, and the second rotary gear 266b is affixed to the second axle 268b adjacent the base (i.e., the circular plane surface) of the second cone 260b, alternatively, the first rotary gear 266a may be affixed to the first axle 268a adjacent the vertex of the first cone 260a, and the second rotary gear 266b may be affixed to the second axle 268b adjacent the vertex of the second cone 260b.

The mechanical transmission linkage 18c(1) further comprises a frame 270 in which the cones 260a, 260b and linear gears 264a, 264b are affixed. The cones 260a, 260b are capable of being rotatably translated about their axes relative to the frame 270, whereas the linear gears 264a, 264b are capable of being linearly translated along their axes relative to the frame 270. The opposing ends of the first axle 268a are rotatably disposed within holes 274a formed in opposing walls 272a, 272b of the frame 270, and the opposing ends of the second axle 268b are rotatably disposed within holes 274b formed in the opposing walls 272a, 272b of the frame 270. The first linear gear 264a and second linear gear 264b respectively slide along the interior of the opposing walls 272a, 272b of the frame 270.

The control mechanism 16 is configured for applying an input force F, and in particular a tensile input, to the belt 262. In the illustrated embodiment, the control mechanism 16 is a variation of the control mechanism 16 illustrated in FIGS. 6A and 6B. In particular, the control mechanism 16 illustrated in FIGS. 18-22 comprises a slider 276 to which the proximal end of the belt 262 is affixed, and a screw mechanism 278 rotatably engaged with a threaded hole (not shown) in the slider 276. As will be described in further detail below, the proximal end of the belt 262 is slidably engaged with the slider 262 to facilitate lateral displacement of the belt 262 between the cones 260a, 260b. The frame 270 comprises two slots 280 formed in the respective walls 272a, 272b in which opposing ends of the slider 276 slide. The collar sleeve 48 of the control mechanism 16 is affixed to the proximal end of the screw mechanism 278, such that rotational displacement of the control mechanism 16 finely displaces the slider 276 linearly along the slots 280 of the opposing walls 272a, 272b of the frame 270, and linear displacement of the control mechanism 16 coarsely displaces the slider 276 linearly along the slots 280 of the opposing walls 272a, 272b of the frame 270.

The belt 262, which is frictionally engaged between the cones 260a, 260b, is linearly displaced (shown by the arrow 282), such that first cone 260a and the first rotary gear 266a rotate in unison (shown by the arrow 284a) to linearly displace the first linear gear 264a, thereby applying the first linear displacement output $D_a$ to the proximal end of the first pull wire 20a, and the second cone 260b and the second rotary gear 266b rotate in unison (shown by the arrow 284b) to linearly displace the second linear gear 264b, thereby applying the second linear displacement output $D_b$ to the proximal end of the second pull wire 20b, in accordance with the preset pull wire displacement ratio.

The preset pull wire displacement ratio of the mechanical transmission linkage 18c(1) illustrated in FIGS. 18-24 (i.e., the ratio between the linear displacement outputs $D_a$, $D_b$) is defined in equation [9] above. The belt 262 is frictionally disposed between the first cone 260a and the second cone 260b at a location coincident with a radius $r_a$ of the first cone 260a and a radius $r_b$ of the second cone 260b (see FIGS. 23A, 23B, 24A, and 24B). Depending upon the lateral location of the belt 262 between the cones 260a, 260b, the cones 260, 260b rotate at respective angular displacements $\alpha_a$, $\alpha_b$. Although the radii R of the rotary gears 266a, 226b are the same, the radius $r_a$ of the first cone 260a is different than the radius $r_b$ of the second cone 260 at the first lateral location of the belt 262 between the cones 260a, 260b. Thus, the preset pull wire linear displacement ratio of the first linear displacement $D_a$ over the second linear displacement $D_b$ will be different than unity. In this embodiment, the angular displacement $\alpha_a$ of the first cone 260a, and thus the first rotary gear 266a, is greater than the angular displacement $\alpha_b$ of the second cone 260a, and thus the second rotary gear 266b, in which case, the preset pull wire linear displacement ratio of the first linear displacement $D_a$ over the second linear displacement $D_b$ will be greater than unity. In alternative embodiments, the angular displacement $\alpha_a$ of the first cone 260a, and thus the first rotary gear 266a, may be less than the angular displacement $\alpha_b$ of the second cone 260a, and thus the second rotary gear 266b, in which case, the preset pull wire linear displacement ratio of the first linear displacement $D_a$ over the second linear displacement $D_b$ may be less than unity.

In the illustrated embodiment, the preset pull wire tension ratio of the mechanical transmission linkage 18c(1) is adjustable. In particular, the angular displacements $\alpha_a$, $\alpha_b$ of the cones 260a, 260b (and thus the rotary gears 266a, 266b) is adjustable. As best shown in FIGS. 18-22, the mechanical transmission linkage 18c(1) further comprises a pull wire displacement ratio adjustment mechanism 22c configured for adjusting the angular displacements $\alpha_a$, $\alpha_b$ of the cones 260a, 260b (and thus the rotary gears 266a, 266b) in an inversely proportional manner.

Figure 23A:
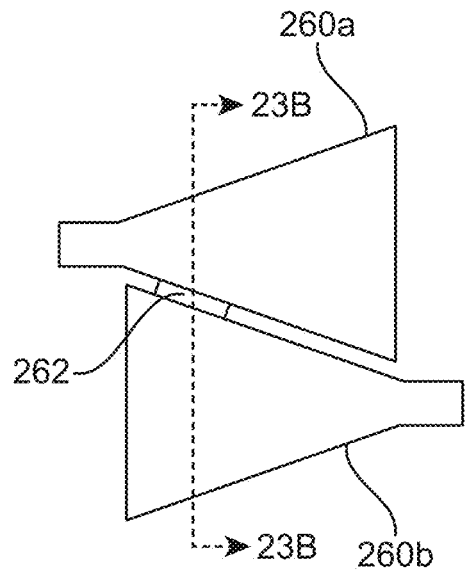
FIG. 23A is a front view of a conical drive used in the mechanical transmission linkage of FIG. 18, particularly showing a belt of the conical drive in one lateral position.
Figure 24A:
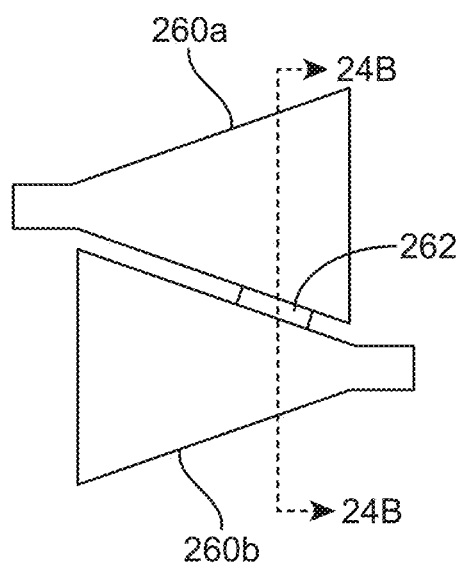
FIG. 24A is a front view of the conical drive of FIG. 23A, particularly showing the belt of conical drive in another lateral position.

To this end, the pull wire displacement ratio adjustment mechanism 22c is configured for laterally sliding the belt 262 between the cones 260a, 260b, e.g., between a first lateral position (see FIG. 23A) and a second lateral position (see FIG. 24A). In the illustrated embodiment, the pull wire displacement ratio adjustment mechanism 22c comprises a pivotable carriage 284 having a plurality of arms 286 that support the belt 262 in tension. In the illustrated embodiment, the pivotable frame has four arms 286a-286d, with the proximal-most arm 286a supporting the proximal end of the belt 262, a distal-most arm 286d supporting the distal end of a spring 288 coupled to the distal end of the belt 262, and middle arms 286b, 286b supporting the middle of the belt 262 just proximal and distal to the cones 260a, 260b.

Figure 19:
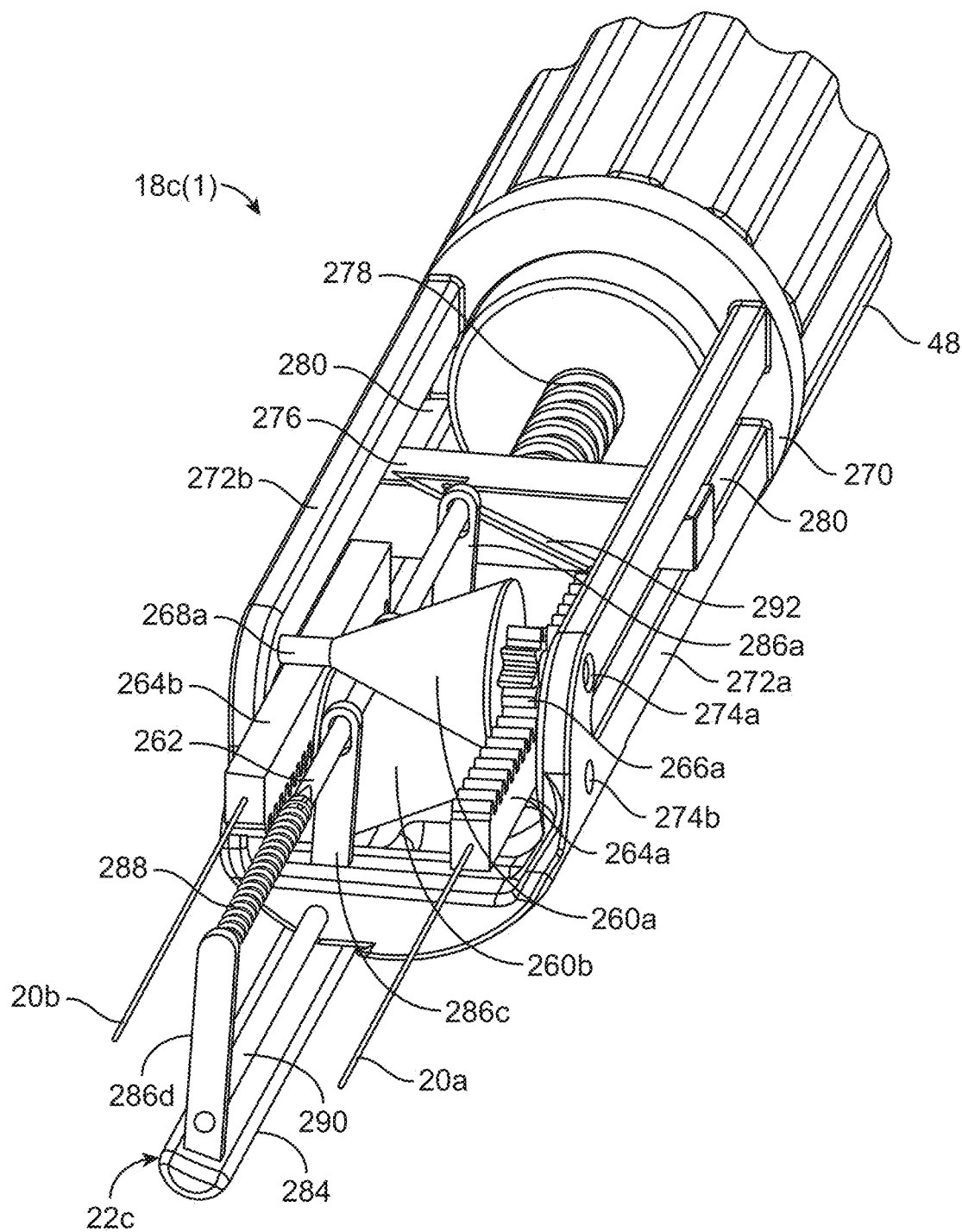
FIG. 19 is a perspective view of the mechanical transmission linkage of FIG. 18.
Figure 22:
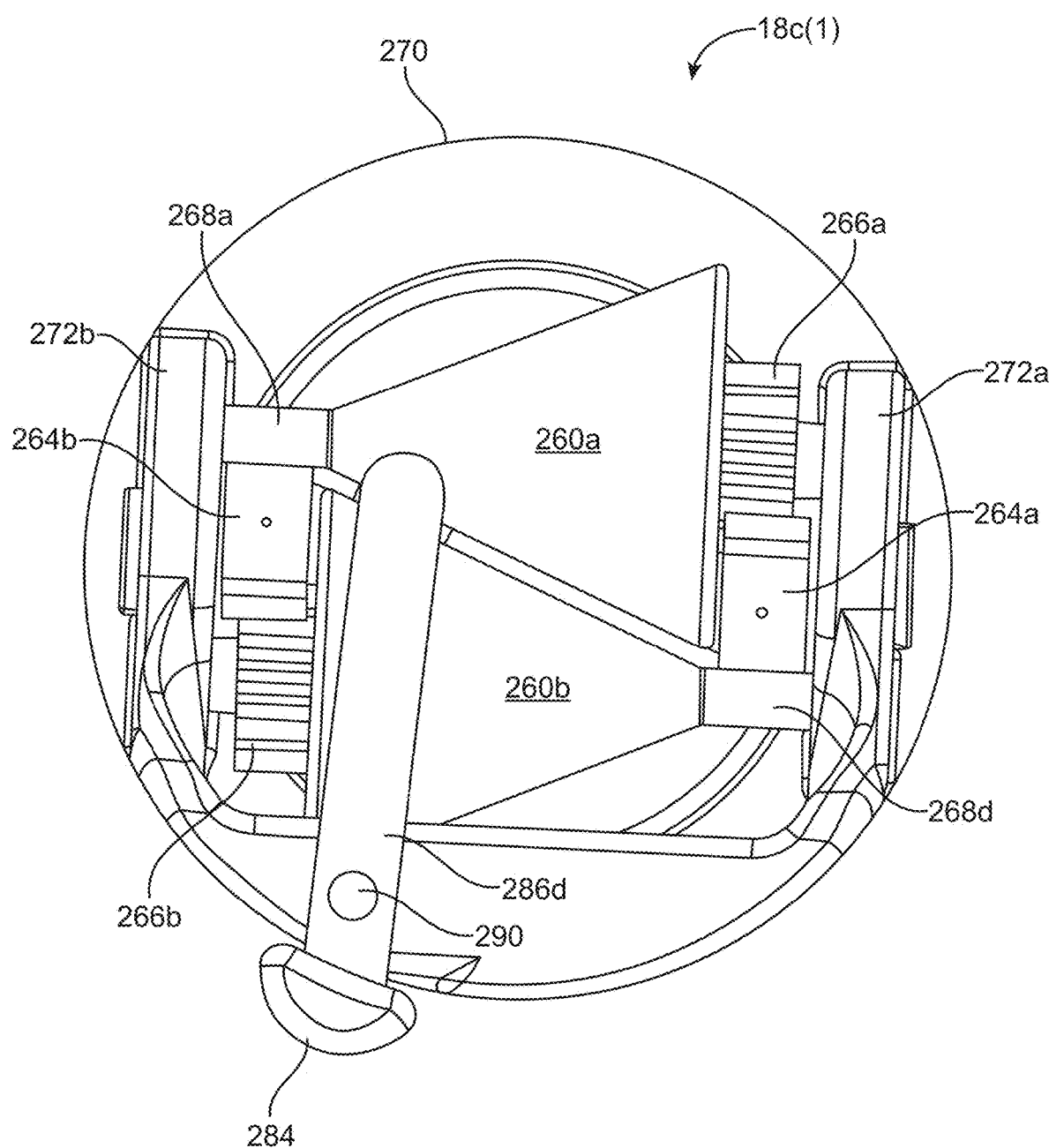
FIG. 22 is a front view of the mechanical transmission linkage of FIG. 18.

The pull wire displacement ratio adjustment mechanism 22c further comprises a pivot arm 290 that extends longitudinally through a bore (not shown) formed through the frame 270, such that the carriage 284 may pivot about the pivot arm 290. The pivot arm 290 extends in a direction along the length of the belt 262, such that the belt 262 is laterally displaced between the cones 260a, 260b when the carriage 284 pivots about the pivot arm 290. As best shown in FIG. 19, the slider 276 of the control mechanism 16 includes a guide slot 292 having an angle that corresponds to the angle of the interface between the cones 260a, 260b. The proximal end of the belt 262 is slidably disposed within the guide slot 292 of the slider 276, thereby allowing the belt 262 to be laterally displaced relative to the slider 276 when the carriage 284 is pivoted about the pivot arm 290. As a result, the angular displacement $\alpha_a$ of the first rotary gear 266a is modified, such that the first pull wire displacement $D_a$ changes, while the angular displacement $\alpha_b$ of the second rotary gear 266b is modified in inverse proportion to the modified angular displacement $\alpha_a$ of the first rotary gear 266a, such that the second pull wire displacement $D_b$ is modified in inverse proportion to the first pull wire displacement $D_a$.

Figure 24B:
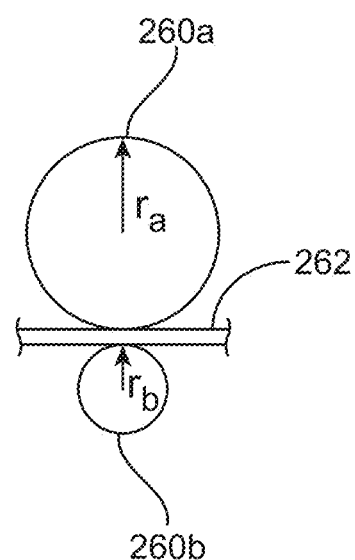
FIG. 24B is a cross-sectional view of the conical drive of FIG. 24A, taken along the line 24B-24B.

For example, when the belt 262 is slid between the cones 260a, 260b (downward along the arrow 294a in FIG. 20), the radius $r_a$ of the first cone 260a coincident with the modified lateral location is increased, thereby decreasing the angular displacement $\alpha_a$ of the first rotary gear 266a and correspondingly decreasing the first pull wire displacement $D_a$, while the radius $r_b$ of the second cone 260b coincident with the modified lateral location is decreased, thereby increasing the angular displacement $\alpha_b$ of the second rotary gear 266b and correspondingly increasing the second pull wire displacement $D_b$ (see, e.g., FIGS. 24A and 24B).

Figure 23B:
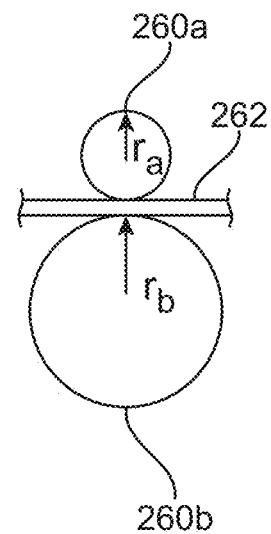
FIG. 23B is a cross-sectional view of the conical drive of FIG. 23A, taken along the line 23B-23B.

In contrast, when the belt 262 is slid between the cones 260a, 260b (upward along the arrow 294b in FIG. 20), the radius $r_a$ of the first cone 260a coincident with the modified lateral location is decreased, thereby increasing the angular displacement $\alpha_a$ of the first rotary gear 266a and correspondingly increasing the first pull wire displacement $D_a$, while the radius $r_b$ of the second cone 260b coincident with the modified lateral location is increased, thereby decreasing the angular displacement $\alpha_b$ of the second rotary gear 266b and correspondingly decreasing the second pull wire displacement $D_b$ (see, e.g., FIGS. 23A and 23B).

As briefly discussed above, the energy transmission linkage 18 may alternatively be a fluid energy transmission linkage, and the single energy input applied to the fluid energy transmission linkage by the control mechanism 16 may be a single mechanical energy input. The energy transmission conduits 20 may be, e.g., mechanical energy transmission conduits, in which case, the energy outputs applied to the mechanical energy transmission conduits by the fluid energy transmission linkage may be mechanical energy outputs, or the energy transmission conduits 20 may be, e.g., fluid energy transmission conduits, in which case, the energy outputs applied to the fluid energy transmission conduits by the fluid energy transmission linkage may be fluid energy outputs.

Figure 25:
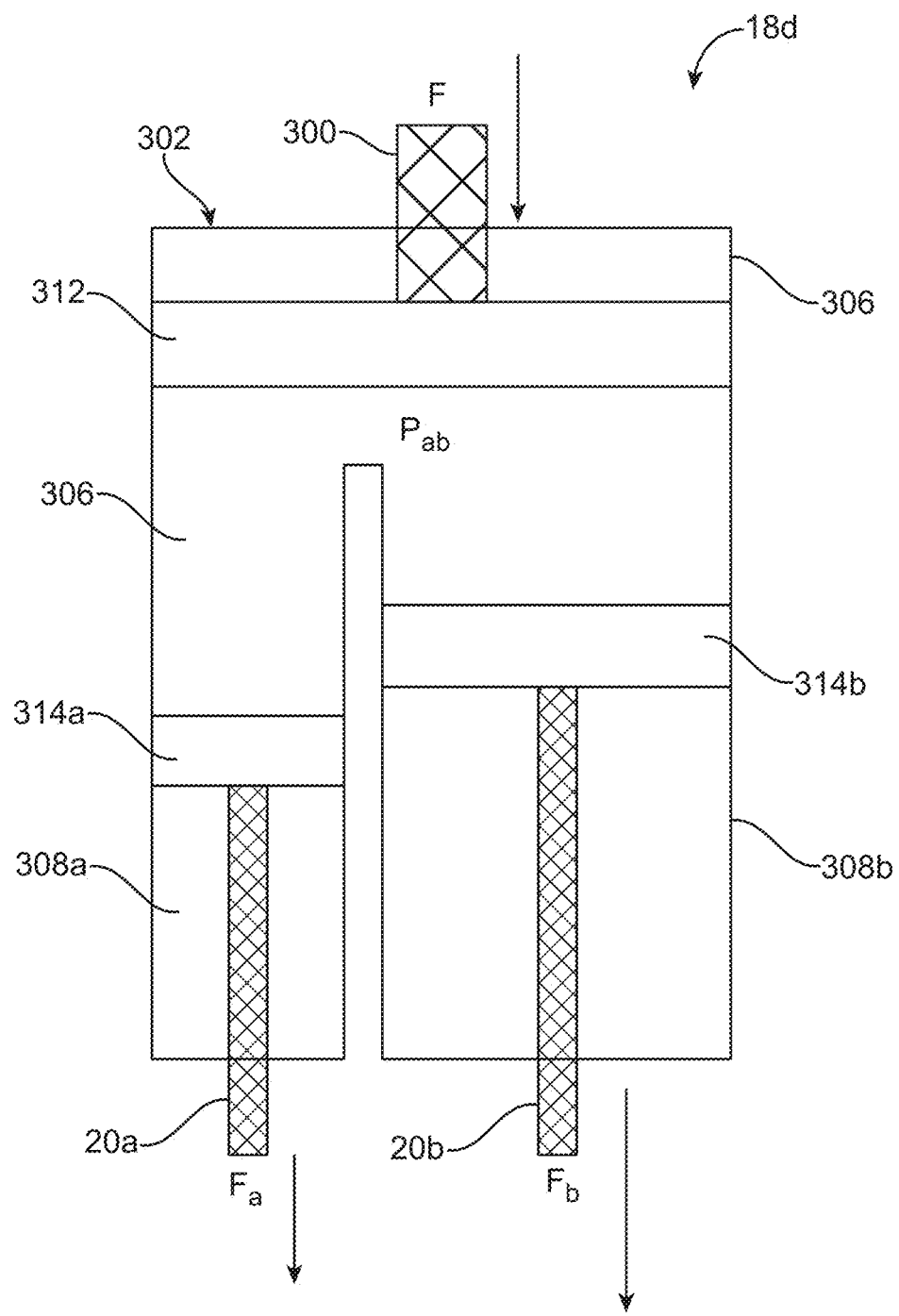
FIG. 25 is a plan view of an embodiment of a fluidic transmission linkage that can alternatively be used in the catheter of FIG. 1A.

Referring to FIG. 25, one exemplary embodiment of a fluidic energy transmission linkage 18d will be described. The fluidic energy transmission linkage 18d is configured for, in response to a mechanical input force F by the control mechanism 16 (shown in FIG. 1), simultaneously applying mechanical outputs Fa, Fb respectively to the proximal ends of two energy transmission conduits 20a, 20b in accordance with a preset mechanical force ratio. In this case, the mechanical input force F by the control mechanism 16 via an input shaft 300, and the energy transmission conduits 20a, 20b are mechanical transmission conduits that take the form of axially rigid, but laterally flexible, rods.

The fluidic energy transmission linkage 18d comprises a bifurcated chamber 302 containing a liquid 304 at a pressure $P_{ab}$. The bifurcated chamber 302 comprises an input chamber portion 306 and a first chamber portion 308a and a second chamber portion 308b that bifurcate from the input chamber portion 306. The input chamber portion 306 and output chamber portions 308a, 308b that are all in fluid communication via a liquid 304, and thus, are at the same pressure $P_{ab}$. The fluidic energy transmission linkage 18d further comprises an input plunger 312 affixed to the distal end of the input rod 300, and slidably disposed within the input chamber portion 306, a first output plunger 314a affixed to the proximal end of the first mechanical transmission conduit 20a, and slidably disposed within the first output chamber portion 308a, and a second output plunger 314b affixed to the proximal end of the second mechanical transmission conduit 20b, and slidably disposed within the second output chamber portion 308a.

The input plunger 312 sealingly engages the walls of the input chamber portion 306, while the output plungers 314a, 314b sealingly engage the walls of the respective output chamber portions 308a, 308b, such that downward displacement of the input plunger 312 in the input chamber portion 306 increases the pressure $P_{ab}$ in the input chamber portion 306, and thus, increases the pressure $P_{ab}$ in the bifurcated output chamber portions 308a, 308b, while upward displacement of the input plunger 312 in the input chamber portion 306 decreases the pressure $P_{ab}$ in the input chamber portion 306, and thus, decreases the pressure $P_{ab}$ in the bifurcated output chamber portions 308a, 308b.

As a result, the output plungers 314a, 314b apply force outputs Fa, Fb to the proximal ends of the mechanical transmission conduits 20a, 20b in accordance with a ratio between the areas of the output plungers 314a, 314b. In the illustrated embodiment, the area of the second output plunger 314b is greater than the area of the first output plunger 314a, and thus, the force output Fb applied to the second mechanical transmission conduit 20b will be greater than the force output Fa applied to the first mechanical transmission conduit 20a. Of course, if the area of the first output plunger 314a is greater than the area of the second output plunger 314b, the force output Fa applied to the first mechanical transmission conduit 20a will be greater than the force output Fb applied to the second mechanical transmission conduit 20b.

Figure 26:
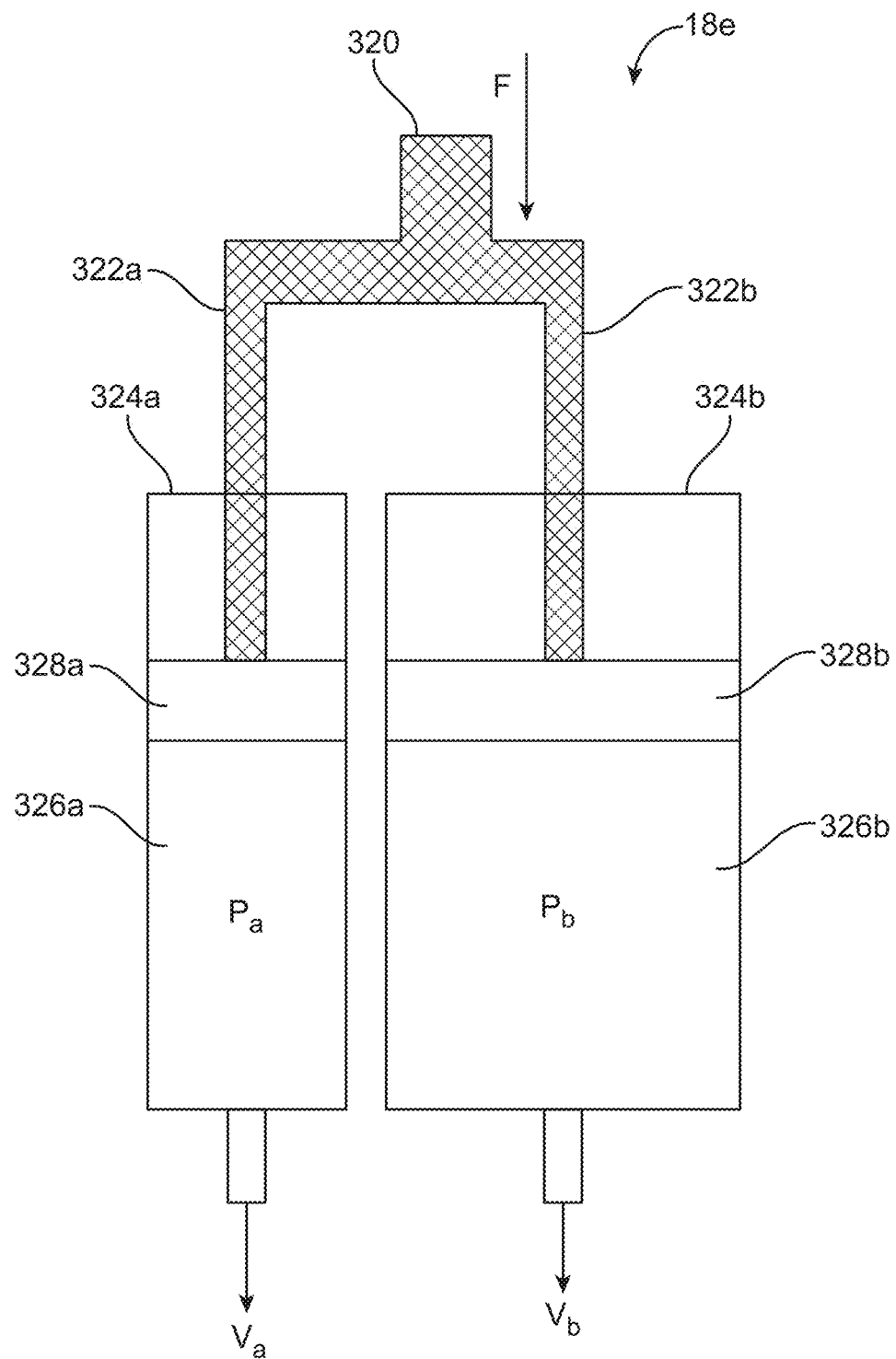
FIG. 26 is a plan view of another embodiment of a fluidic transmission linkage that can alternatively be used in the catheter of FIG. 1A.

Referring to FIG. 26, another exemplary embodiment of a fluidic energy transmission linkage 18e will be described. The fluidic energy transmission linkage 18e is configured for, in response to a mechanical input force F by the control mechanism 16 (shown in FIG. 1), simultaneously applying volume outputs $V_a$, $V_b$ respectively to the proximal ends of two mechanical transmission conduits 20a, 20b in accordance with a preset fluid volume ratio. In this case, the mechanical input force F by the control mechanism 16 via a yoke 320 having a first arm 322a and a second arm 322b, and the energy transmission conduits 20a, 20b are fluidic transmission conduits that take the form of hydraulic lines.

The fluidic energy transmission linkage 18d comprises a first chamber 324a containing liquid 326a at a first pressure Pa, and a second chamber 324b containing liquid 326b at a second pressure Pb. The chambers 324a, 324b are fluidly isolated from each other, and thus, the pressures Pa, Pb are independent of each other. The fluidic energy transmission linkage 18e further comprises a first plunger 328a affixed to the distal end of the first arm 322a of the yoke 320, and slidably disposed within the first chamber 324a, and a second plunger 328b affixed to the distal end of the second arm 322b of the yoke 320, and slidably disposed within the second chamber 324b.

The first plunger 328a sealingly engages the walls of the first chamber 324a, while the second plunger 328b sealingly engage the walls of the second chamber 324b, such that downward displacement of the plunger 328a, 328b in the chambers 324a, 324b increases the pressures Pa, Pb in the chambers 324a, 324b, while upward displacement of the plunger 328a, 328b in the chambers 324a, 324b decreases the pressures Pa, Pb in the chambers 324a, 324b. The pressures Pa, Pb in the respective chambers 324a, 324b will be proportional to the areas of the output plunger 328a, 328b.

As a result, the plunger 328a, 328b apply volume outputs $V_a$, $V_b$ to the proximal ends of the fluidic transmission conduits 20a, 20b in accordance with a ratio between the areas of the output plunger 328a, 328b. In the illustrated embodiment, the area of the second plunger 328b is greater than the area of the first plunger 328a, and thus, the volume output $V_b$ applied to the second fluidic transmission conduit 20b will be greater than the volume output $V_a$ applied to the first fluidic transmission conduit 20a. Of course, in the case where the area of the first plunger 328a is greater than the area of the second plunger 328b, the volume output $V_a$ applied to the first fluidic transmission conduit 20a will be greater than the volume output $V_b$ applied to the second fluidic transmission conduit 20b.

Although particular embodiments have been shown and described herein, it will be understood by those skilled in the art that they are not intended to limit the disclosed inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed is:

1. An intravascular device, comprising:
   an elongated catheter body having a proximal end and a distal end;
   first and second pull wires extending within the elongated catheter body, wherein distal ends of the first and second pull wires terminate at different axial locations along the distal end of the catheter body;
   a pulley including an axle and a wheel around which a proximal end of the first pull wire is looped;
   a lever arm to which a proximal end of the looped first pull wire is engaged at a first anchor point, and to which a proximal end of the second pull wire is engaged at a second anchor point different from the first anchor point;
   a controller configured for applying a single linear tensile force to the pulley, whereby two tensile outputs are simultaneously applied respectively to the proximal ends of the first and second pull wires by the lever arm at the first and second anchor points in accordance with a preset pull wire tension ratio, such that the distal end of the elongated catheter body assumes a compound curve comprising two bends.

2. The intravascular device of claim 1, further comprising a handle affixed to the proximal end of the elongated catheter body, wherein the controller, pulley, and lever arm are supported by the handle.

3. The intravascular device of claim 1, wherein the first anchor point is located between the second anchor point and a hinge of the lever arm, such that the preset pull wire tension ratio of the first tensile output over the second tensile output is greater than unity.

4. The intravascular device of claim 3, wherein the proximal end of the first pull wire is slidably engaged to the lever arm, such that the first anchor point is adjustable along a length of the lever arm to adjust the preset pull wire tension ratio of the first tensile output over the second tensile output.

5. The intravascular device of claim 4, further comprising a wire tension ratio adjustment mechanism configured for adjusting the first anchor point along the length of the lever arm.

6. The intravascular device of claim 5, wherein the wire tension ratio adjustment mechanism comprises a slider carriage to which the proximal end of the first pull wire is affixed, the slider carriage configured for being displaced along the lever arm to adjust the first anchor point along the length of the lever arm.

7. The intravascular device of claim 6, wherein the lever arm has a lengthwise slot and the slider carriage has a protuberance to which the proximal end of the first pull wire is affixed, the protuberance configured for slidably engaging the slot of the lever arm.

8. The intravascular device of claim 6, wherein the slider carriage comprises first and second collars transversely straddling the lever arm, and the wire tension ratio adjustment mechanism further comprises a first rod and a second rod respectively threadedly engaged in the first collar and the second collar of the slider carriage, a drive gear affixed to the first rod, and an idle gear affixed to the second rod, the drive gear and the idle gear being engaged with each other, such that rotation of the first rod causes the second rod to rotate via the engagement between the drive gear and the idle gear, thereby displacing the slider carriage along the lever arm.

9. The intravascular device of claim 1, further comprises further comprising a yoke having two arms, the axle of the pulley being rotatably affixed between the two arms of the yoke, and the controller being coupled to the yoke for applying the single linear tensile force to the axle of the pulley.

10. The intravascular device of claim 1, wherein the preset pull wire ratio is uniform through a range of different single linear tensile forces applied by the controller to the pulley.

* * * * *